US006974411B2

(12) United States Patent
Belson

(10) Patent No.: US 6,974,411 B2
(45) Date of Patent: Dec. 13, 2005

(54) ENDOSCOPE WITH SINGLE STEP GUIDING APPARATUS

(75) Inventor: Amir Belson, Cupertino, CA (US)

(73) Assignee: Neoguide Systems, Inc., Los Gatos, CA (US)

( * ) Notice: Subject to any disclaimer, the term of this patent is extended or adjusted under 35 U.S.C. 154(b) by 91 days.

(21) Appl. No.: 10/229,814

(22) Filed: Aug. 27, 2002

(65) Prior Publication Data

US 2003/0032859 A1 Feb. 13, 2003

Related U.S. Application Data

(63) Continuation-in-part of application No. 10/087,100, filed on Mar. 1, 2002, now Pat. No. 6,800,056, which is a continuation-in-part of application No. 09/969,927, filed on Oct. 2, 2001, now Pat. No. 6,610,007, which is a continuation-in-part of application No. 09/790,204, filed on Feb. 20, 2001, now Pat. No. 6,468,203.
(60) Provisional application No. 60/194,140, filed on Apr. 3, 2000.

(51) Int. Cl.$^7$ ................................................ A61B 1/00
(52) U.S. Cl. ...................................................... 600/114
(58) Field of Search ................................ 600/114, 115, 600/139, 144, 145, 146

(56) References Cited

U.S. PATENT DOCUMENTS

| 616,672 A | 12/1898 | Kelling |
| 2,510,198 A | 6/1950 | Tesmer |
| 2,533,494 A | 12/1950 | Mitchell, Jr. |
| 2,767,705 A | 10/1956 | Moore |
| 3,060,972 A | 10/1962 | Sheldon |
| 3,096,962 A | 7/1963 | Meijs |
| 3,162,214 A | 12/1964 | Bazinet, Jr. |
| 3,168,274 A | 2/1965 | Street |

(Continued)

FOREIGN PATENT DOCUMENTS

| DE | 28 23 025 | 12/1979 |
| DE | 37 07 787 | 9/1988 |
| EP | 0 497 781 B1 | 8/1992 |
| FR | 2732225 A1 | 10/1996 |
| JP | 63 136014 | 6/1988 |
| JP | 111458 A | 5/1993 |
| JP | 5-1999 A | 10/1993 |
| WO | WO 93/17751 A1 | 3/1993 |

(Continued)

OTHER PUBLICATIONS

U.S. Appl. No. 09/556,673, filed Apr. 21, 2001, Francois et al.
Hasson, II.M, (May. 1979), Technique of Open Laparoscopy: Equipment and Technique (from step 1 to step 9), 2424 North Clark Street, Chicago, Illinois 60614, 3 pages.
McKernan, "History: Laparoscopic General Surgery: from 1983 to Apr. 11, 1989," 4 pages.

(Continued)

Primary Examiner—Beverly M. Flanagan
(74) Attorney, Agent, or Firm—Wilson Sonsini Goodrich & Rosati

(57) ABSTRACT

An endoscope with guiding apparatus is described herein. A steerable endoscope is described having an elongate body with a manually or selectively steerable distal portion, an automatically controlled portion, a flexible and passively manipulated proximal portion, and an externally controlled and manipulatable tracking rod or guide. The tracking rod or guide is positioned within a guide channel within the endoscope and slides relative to the endoscope. When the guide is in a flexible state, it can conform to a curve or path defined by the steerable distal portion and the automatically controlled portion. The guide can then be selectively rigidized to assume that curve or path. Once set, the endoscope can be advanced over the rigidized guide in a monorail or "piggyback" fashion so that the flexible proximal portion follows the curve held by the guide until the endoscope reaches a next point of curvature within a body lumen.

33 Claims, 18 Drawing Sheets

U.S. PATENT DOCUMENTS

| | | |
|---|---|---|
| 3,430,662 A | 3/1969 | Guarnaschelli |
| 3,546,961 A | 12/1970 | Marton |
| 3,610,231 A | 10/1971 | Takahashi et al. |
| 3,643,653 A | 2/1972 | Takahashi et al. |
| 3,739,770 A | 6/1973 | Mori |
| 3,773,034 A | 11/1973 | Burns et al. |
| 3,858,578 A | 1/1975 | Milo |
| 3,897,775 A | 8/1975 | Furihata |
| 3,913,565 A | 10/1975 | Kawahara |
| 3,946,727 A | 3/1976 | Okada et al. |
| 4,054,128 A | 10/1977 | Seufert et al. |
| 4,176,662 A | 12/1979 | Frazer |
| 4,236,509 A | 12/1980 | Takahashi et al. |
| 4,240,435 A | 12/1980 | Yazawa et al. |
| 4,273,111 A | 6/1981 | Tsukaya |
| 4,327,711 A | 5/1982 | Takagi |
| 4,366,810 A | 1/1983 | Slanetz, Jr. |
| 4,432,349 A | 2/1984 | Oshiro |
| 4,499,895 A | 2/1985 | Takayama |
| 4,503,842 A | 3/1985 | Takayama |
| 4,543,090 A | 9/1985 | McCoy |
| 4,559,928 A | 12/1985 | Takayama |
| 4,577,621 A | 3/1986 | Patel |
| 4,592,341 A | 6/1986 | Omagari et al. |
| 4,601,283 A | 7/1986 | Chikama |
| 4,621,618 A | 11/1986 | Omagari |
| 4,624,243 A | 11/1986 | Lowery et al. |
| 4,646,722 A | 3/1987 | Silverstein et al. |
| 4,648,733 A | 3/1987 | Merkt |
| 4,651,718 A | 3/1987 | Collins et al. |
| 4,655,257 A | 4/1987 | Iwashita |
| 4,686,963 A | 8/1987 | Cohen et al. |
| 4,753,223 A | 6/1988 | Bremer |
| 4,788,967 A | 12/1988 | Ueda |
| 4,793,326 A | 12/1988 | Shishido |
| 4,799,474 A | 1/1989 | Ueda |
| 4,815,450 A | 3/1989 | Patel |
| 4,832,473 A | 5/1989 | Ueda |
| 4,834,068 A | 5/1989 | Gottesman |
| 4,873,965 A | 10/1989 | Danieli |
| 4,873,990 A | 10/1989 | Holmes et al. |
| 4,879,991 A | 11/1989 | Ogiu |
| 4,884,557 A | 12/1989 | Takehana et al. |
| 4,890,602 A | 1/1990 | Hake |
| 4,895,431 A | 1/1990 | Tsujiuchi et al. |
| 4,899,731 A | 2/1990 | Takayama et al. |
| 4,904,048 A | 2/1990 | Sogawa et al. |
| 4,930,494 A | 6/1990 | Takehana et al. |
| 4,949,927 A | 8/1990 | Madocks et al. |
| 4,957,486 A | 9/1990 | Davis |
| 4,969,709 A | 11/1990 | Sogawa et al. |
| 4,971,035 A | 11/1990 | Ito |
| 4,977,887 A | 12/1990 | Gouda |
| 4,987,314 A | 1/1991 | Gotanda et al. |
| 5,018,509 A | 5/1991 | Suzuki et al. |
| 5,060,632 A | 10/1991 | Hibino et al. |
| 5,092,901 A | 3/1992 | Hunter et al. |
| 5,125,395 A | 6/1992 | Adair |
| 5,127,393 A | 7/1992 | McFarlin et al. |
| 5,159,446 A | 10/1992 | Hibino et al. |
| 5,174,276 A | 12/1992 | Crockard |
| 5,174,277 A | 12/1992 | Matsumaru |
| 5,188,111 A | 2/1993 | Yates et al. |
| 5,217,001 A | 6/1993 | Nakao et al. |
| 5,220,911 A | 6/1993 | Tamura |
| 5,243,967 A | 9/1993 | Hibino |
| 5,251,611 A | 10/1993 | Zehel et al. |
| 5,257,617 A | 11/1993 | Takahashi |
| 5,271,381 A | 12/1993 | Ailinger et al. |
| 5,325,845 A | 7/1994 | Adair |
| 5,337,732 A | 8/1994 | Grundfest et al. |
| 5,337,733 A | 8/1994 | Bauerfeind et al. |
| 5,348,259 A | 9/1994 | Blanco et al. |
| 5,370,108 A | 12/1994 | Miura et al. |
| 5,383,852 A | 1/1995 | Stevens-Wright |
| 5,389,222 A | 2/1995 | Shahinpoor |
| 5,394,864 A | 3/1995 | Kobayashi et al. |
| 5,400,769 A | 3/1995 | Tanii et al. |
| 5,402,768 A | 4/1995 | Adair |
| 5,429,118 A | 7/1995 | Cole et al. |
| 5,460,166 A | 10/1995 | Yabe et al. |
| 5,460,168 A | 10/1995 | Masubuchi et al. |
| 5,469,840 A | 11/1995 | Tanii et al. |
| 5,482,029 A | 1/1996 | Sekiguchi et al. |
| 5,487,757 A | 1/1996 | Truckai et al. |
| 5,507,717 A | 4/1996 | Kura et al. |
| 5,531,664 A | 7/1996 | Adachi et al. |
| 5,551,945 A | 9/1996 | Yabe et al. |
| 5,558,619 A | 9/1996 | Kami et al. |
| 5,558,665 A | 9/1996 | Kieturakis |
| 5,577,992 A | 11/1996 | Chiba et al. |
| 5,620,408 A | 4/1997 | Vennes et al. |
| 5,624,380 A | 4/1997 | Takayama et al. |
| 5,624,381 A | 4/1997 | Kieturakis |
| 5,626,553 A | 5/1997 | Frassica et al. |
| 5,645,520 A | 7/1997 | Nakamura et al. |
| 5,658,238 A | 8/1997 | Suzuki et al. |
| 5,662,587 A | 9/1997 | Grundfest et al. |
| 5,665,050 A | 9/1997 | Benecke |
| 5,667,476 A | 9/1997 | Frassica et al. |
| 5,679,216 A | 10/1997 | Takayama et al. |
| 5,728,044 A | 3/1998 | Shan |
| 5,733,245 A | 3/1998 | Kawano |
| 5,749,828 A | 5/1998 | Solomon et al. |
| 5,752,912 A | 5/1998 | Takahashi et al. |
| 5,759,151 A | 6/1998 | Sturges |
| 5,779,624 A | 7/1998 | Chang |
| 5,807,241 A | 9/1998 | Heimberger |
| 5,810,715 A | 9/1998 | Moriyama |
| 5,842,973 A | 12/1998 | Bullard |
| 5,860,914 A | 1/1999 | Chiba et al. |
| 5,876,329 A | 3/1999 | Harhen |
| 5,876,373 A | 3/1999 | Giba et al. |
| 5,885,208 A | 3/1999 | Moriyama |
| 5,897,417 A | 4/1999 | Grey |
| 5,897,488 A | 4/1999 | Ueda |
| 5,902,254 A | 5/1999 | Magram |
| 5,906,591 A | 5/1999 | Dario et al. |
| 5,908,381 A | 6/1999 | Aznoian et al. |
| 5,911,715 A | 6/1999 | Berg et al. |
| 5,916,147 A | 6/1999 | Boury |
| 5,921,915 A | 7/1999 | Aznoian et al. |
| 5,928,136 A | 7/1999 | Barry |
| 5,941,815 A | 8/1999 | Chang |
| 5,957,833 A | 9/1999 | Shan |
| 5,976,074 A | 11/1999 | Moriyama |
| 5,989,182 A | 11/1999 | Hori et al. |
| 5,989,230 A | 11/1999 | Frassica |
| 5,993,381 A | 11/1999 | Ito |
| 5,996,346 A | 12/1999 | Maynard |
| 6,036,636 A | 3/2000 | Motoki et al. |
| 6,042,155 A | 3/2000 | Lockwood |
| 6,048,307 A | 4/2000 | Grundl et al. |
| 6,066,132 A | 5/2000 | Chen et al. |
| 6,099,464 A | 8/2000 | Shimizu et al. |
| 6,099,485 A | 8/2000 | Patterson |
| 6,106,510 A | 8/2000 | Lunn et al. |
| 6,149,581 A | 11/2000 | Klingenstein |
| 6,162,171 A | 12/2000 | Ng et al. |
| 6,174,280 B1 | 1/2001 | Oneda et al. |
| 6,179,776 B1 | 1/2001 | Adams et al. |

| | | |
|---|---|---|
| 6,210,337 B1 | 4/2001 | Dunham et al. |
| 6,221,006 B1 | 4/2001 | Dubrul et al. |
| 6,249,076 B1 | 6/2001 | Madden et al. |
| 6,270,453 B1 | 8/2001 | Sakai |
| 6,306,081 B1 | 10/2001 | Ishikawa et al. |
| 6,309,346 B1 | 10/2001 | Farhadi |
| 6,315,714 B1 | 11/2001 | Akiba |
| 6,327,492 B1 | 12/2001 | Lemelson |
| 6,402,687 B1 | 6/2002 | Ouchi |
| 6,408,889 B1 | 6/2002 | Komachi |
| 6,468,203 B2 | 10/2002 | Belson |
| 6,482,149 B1 | 11/2002 | Torii |
| 6,527,706 B2 | 3/2003 | Ide |
| 6,554,793 B1 | 4/2003 | Pauker et al. |
| 6,610,007 B2 | 8/2003 | Tartaglia et al. |
| 6,616,600 B2 | 9/2003 | Pauker |
| 6,638,213 B2 | 10/2003 | Ogura et al. |
| 6,641,528 B2 | 11/2003 | Torii |
| 6,699,183 B1 | 3/2004 | Wimmer |
| 6,761,685 B2 | 7/2004 | Adams et al. |
| 6,783,491 B2 | 8/2004 | Saadat et al. |
| 6,790,173 B2 | 9/2004 | Saadat et al. |
| 6,800,056 B2 | 10/2004 | Tartaglia et al. |
| 2001/0000040 A1 | 3/2001 | Adams et al. |
| 2002/0022765 A1 | 2/2002 | Belson |
| 2002/0062062 A1 | 5/2002 | Belson et al. |
| 2002/0120178 A1 | 8/2002 | Tartaglia et al. |
| 2002/0147385 A1 | 10/2002 | Butler et al. |
| 2002/0161281 A1 | 10/2002 | Jaffe et al. |
| 2002/0193661 A1 | 12/2002 | Belson |
| 2002/0193662 A1 | 12/2002 | Belson |
| 2003/0083550 A1 | 5/2003 | Miyagi |
| 2003/0130598 A1 | 7/2003 | Manning et al. |
| 2003/0149338 A1 | 8/2003 | Francois et al. |
| 2003/0195387 A1 | 10/2003 | Kortenbach et al. |
| 2003/0233027 A1 | 12/2003 | Ewers et al. |
| 2003/0233056 A1 | 12/2003 | Saadat et al. |
| 2003/0233057 A1 | 12/2003 | Saadat et al. |
| 2003/0233058 A1 | 12/2003 | Ewers et al. |
| 2003/0233066 A1 | 12/2003 | Ewers et al. |
| 2003/0236505 A1 | 12/2003 | Bonadio et al. |
| 2003/0236549 A1 | 12/2003 | Bonadio et al. |
| 2004/0044270 A1 | 3/2004 | Barry |
| 2004/0106852 A1 | 6/2004 | Windheuser et al. |
| 2004/0193008 A1 | 9/2004 | Jaffe et al. |
| 2004/0193009 A1 | 9/2004 | Jaffe et al. |
| 2005/0085693 A1 | 4/2005 | Belson et al. |

FOREIGN PATENT DOCUMENTS

| | | |
|---|---|---|
| WO | WO 94/19051 A1 | 9/1994 |
| WO | WO 95/04556 A2 | 3/1995 |
| WO | WO 97/10746 A1 | 3/1997 |
| WO | WO 99/33392 A1 | 7/1999 |
| WO | WO 99/51283 A2 | 10/1999 |
| WO | WO 99/59664 A1 | 11/1999 |
| WO | WO 00/54653 A1 | 9/2000 |
| WO | WO 01/49353 A2 | 7/2001 |
| WO | WO 01/67964 A2 | 9/2001 |
| WO | WO 01/70096 A1 | 9/2001 |
| WO | WO 01/70097 A1 | 9/2001 |
| WO | WO 01/74235 | 10/2001 |
| WO | WO 01/80935 A1 | 11/2001 |
| WO | WO 02/024058 A2 | 3/2002 |
| WO | WO 02/39909 A1 | 5/2002 |
| WO | WO 02/064028 A1 | 8/2002 |
| WO | WO 02/068988 A1 | 9/2002 |
| WO | WO 02/069841 A2 | 9/2002 |
| WO | WO 02/096276 A1 | 12/2002 |
| WO | WO 03/028547 A2 | 4/2003 |
| WO | WO 03/028547 | 4/2003 |
| WO | WO 03/092476 | 11/2003 |
| WO | WO 03/092476 A2 | 11/2003 |
| WO | WO 2004/006980 A2 | 1/2004 |
| WO | WO 2004/049905 A2 | 6/2004 |
| WO | WO 2004/071284 A1 | 8/2004 |
| WO | WO 2004/080313 A1 | 9/2004 |
| WO | WO 2004/084702 A2 | 10/2004 |

OTHER PUBLICATIONS

U.S. Appl. No. 10/229,577, filed Aug. 27, 2002, Belson.

Lee, T.S. et al. (1994). "A Highly Redundant Robot System For Inspection," Proceedings of Conference on Intelligent Robots in Factory, Fields, Space and Service. Houston, TX Mar. 21–24, 1994 Part vol. 1:142–148.

Slatkin et al. (Aug. 1995). "The Development of a Robotic Endoscope ," Proceedings 1995 IEEE/RSJ International Conference on Human Robot Interaction and Cooperative Robots. Pittsburgh, PA Aug. 5–9, 1995, Proceedings of the IEEE/RSJ International Conference on Intelligent Robot Syst. 2:162–171.

Science & Technology, Laptop Magazine: p. 98 (Oct. 2002).

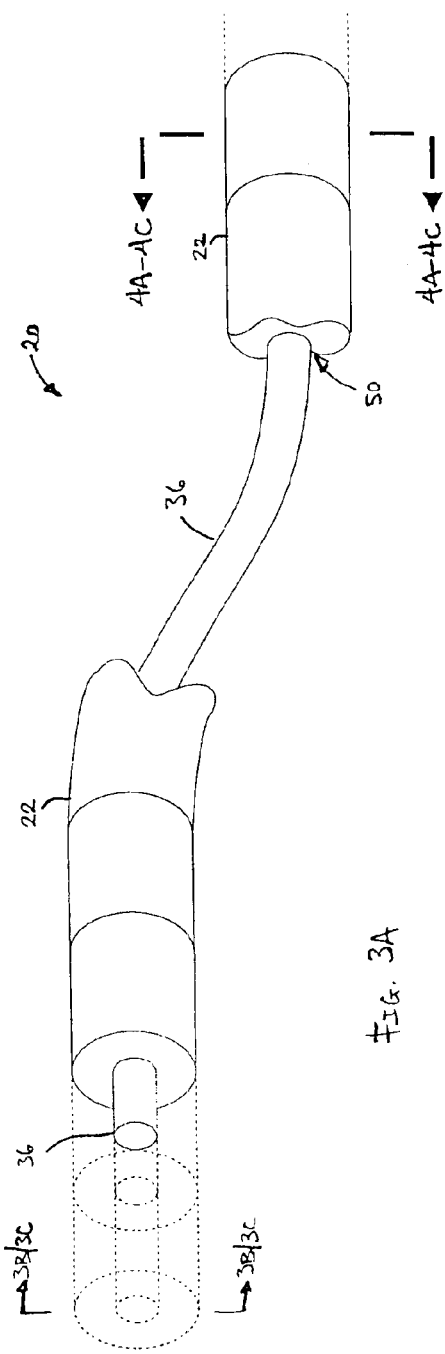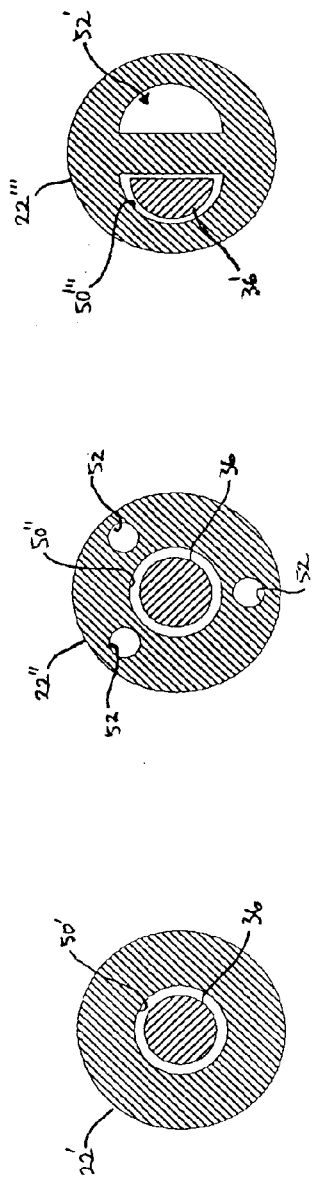

ENDOSCOPE WITH SINGLE STEP GUIDING APPARATUS

CROSS-REFERENCE TO RELATED APPLICATIONS

This application is a continuation-in-part of U.S. patent application Ser. No. 10/087,100 entitled "Endoscope with Guiding Apparatus" filed Mar. 1, 2002, now U.S. Pat. No. 6,800,056 which is a continuation-in-part of U.S. patent application Ser. No. 09/969,927 entitled "Steerable Segmented Endoscope and Method of Insertion" filed Oct. 2, 2001, now U.S. Pat. No. 6,610,007 which is a continuation-in-part of U.S. patent application Ser. No. 09/790,204 entitled "Steerable Endoscope and Improved Method of Insertion" filed Feb. 20, 2001, now U.S. Pat. No. 6,468,203 which claims the benefit of priority to U.S. Provisional Patent Application Ser. No. 60/194,140 entitled the same and filed Apr. 3, 2000, all of which are incorporated herein by reference in their entirety.

FIELD OF THE INVENTION

The present invention relates generally to endoscopes and endoscopic procedures. More particularly, it relates to a method and apparatus to facilitate insertion of a flexible endoscope along a tortuous path, such as for colonoscopic examination and treatment.

BACKGROUND OF THE INVENTION

An endoscope is a medical instrument for visualizing the interior of a patient's body. Endoscopes can be used for a variety of different diagnostic and interventional procedures, including colonoscopy, bronchoscopy, thoracoscopy, laparoscopy and video endoscopy.

Colonoscopy is a medical procedure in which a flexible endoscope, or colonoscope, is inserted into a patient's colon for diagnostic examination and/or surgical treatment of the colon. A standard colonoscope is typically 135–185 cm in length and 12–19 mm in diameter, and includes a fiberoptic imaging bundle or a miniature camera located at the instrument's tip, illumination fibers, one or two instrument channels that may also be used for insufflation or irrigation, air and water channels, and vacuum channels. The colonoscope is inserted via the patient's anus and is advanced through the colon, allowing direct visual examination of the colon, the ileocecal valve and portions of the terminal ileum.

Insertion of the colonoscope is complicated by the fact that the colon represents a tortuous and convoluted path. Considerable manipulation of the colonoscope is often necessary to advance the colonoscope through the colon, making the procedure more difficult and time consuming and adding to the potential for complications, such as intestinal perforation. Steerable colonoscopes have been devised to facilitate selection of the correct path though the curves of the colon. However, as the colonoscope is inserted farther and farther into the colon, it becomes more difficult to advance the colonoscope along the selected path. At each turn, the wall of the colon must maintain the curve in the colonoscope. The colonoscope rubs against the mucosal surface of the colon along the outside of each turn. Friction and slack in the colonoscope build up at each turn, making it more and more difficult to advance, withdraw, and loop the colonoscope. In addition, the force against the wall of the colon increases with the buildup of friction. In cases of extreme tortuosity, it may become impossible to advance the colonoscope all of the way through the colon.

Steerable endoscopes, catheters and insertion devices for medical examination or treatment of internal body structures are described in the following U.S. patents, the disclosures of which are hereby incorporated by reference in their entirety: U.S. Pat. Nos. 4,543,090; 4,753,223; 5,337,732; 5,337,733; 5,383,852; 5,487,757; 5,624,381; 5,662,587; and 5,759,151.

SUMMARY OF THE INVENTION

Accordingly, an improved endoscopic apparatus is disclosed herein for the examination of a patient's colon, other internal bodily cavities, and any other spaces within the body with minimal impingement upon bodily cavities or upon the walls of the organs. The disclosed apparatus may also be employed for various surgical treatments of those regions, e.g., insufflation, drug delivery, biopsies, etc. A steerable endoscope having an elongate body with a manually or selectively steerable distal portion, an automatically controlled portion, which may be optionally omitted from the device, a flexible and passively manipulated proximal portion, and an externally controlled and manipulatable tracking rod or guide is described below. The tracking rod or guide may be slidably positioned within a guide channel or lumen within the endoscope or it may be externally positionable such that the guide and the endoscope may slide relative to one another along a rail or channel located along an external surface of the endoscope.

In operation, the steerable distal portion of the endoscope may be first advanced into a patient's rectum via the anus. The endoscope may be simply advanced, either manually or automatically by a motor, until the first curvature is reached. At this point, the steerable distal portion may be actively controlled by the physician or surgeon to attain an optimal curvature or shape for advancement of the endoscope. The optimal curvature or shape is considered to be the path which presents the least amount of contact or interference from the walls of the colon. In one variation, once the desired curvature has been determined, the endoscope may be advanced further into the colon such that the automatically controlled segments of controllable portion follow the distal portion while transmitting the optimal curvature or shape proximally down the remaining segments of the controllable portion. The operation of the controllable segments will be described in further detail below.

In one variation, the guide is shorter than the full length of the endoscope, e.g., approximately the length of the controllable portion, and this shortened guide can be preloaded through the proximal end of the endoscope or through the handle of the endoscope. Once the guide is inserted, it may be advanced distally through the endoscope to the distal tip of the endoscope. As the user advances the endoscope distally, the automatically controlled segments of the proximal controllable portion propagate the selected curves down the endoscope, and the guide, in its flexible state, passively conforms to the shape of the desired pathway. Once the endoscope has advanced to a desired position, e.g. to a depth less than the length of the controllable portion of the endoscope, the user can rigidize the guide and maintain it at that depth (or axial position). The endoscope can then be further advanced relative to the rigidized guide, sliding over the rigid guide and along the selected pathway. Thus, the surgeon or physician only needs to lock the guide in position once. If the controllable region of the endoscope and the guide are each at least half of the length of the endoscope, the entire endoscope can conform to a selected pathway in this manner. It is also possible to reposition the guide easily by relaxing and/or unlocking it from its rigidized axial position and then moving the guide into its new position.

In an alternative variation, once the steerable distal portion has been steered or positioned for advancement, the guide may be advanced distally in its flexible state along or within the endoscope until it reaches a distal position, i.e., preferably some point distal of the flexible proximal portion. Regardless whether the optional controllable portion is omitted or not from the device, the guide may be advanced near or to the end of the distal portion. Once the guide has been advanced, it may directly attain and conform to the curvature or shape defined by the steerable distal portion.

Preferably, the guide is advanced to the distal end of steerable distal portion or, if the controllable portion is included in the device, the guide may be advanced to the distal end of the controllable portion, or to some point between the two portions. The guide may be advanced to any distal position as long as a portion of guide attains and conforms to the optimal curvature or shape. Prior to advancing the endoscope over the guide, the guide may be left in its flexible state or it may be optionally rigidized, as discussed further below. If left in its flexible state, the guide may possibly provide desirable column strength to the endoscope as it is advanced through the colon over the guide. It is preferable, however, that the guide is rigidized once it has attained and conformed to the curvature. This allows the flexible proximal portion, i.e., the passive portion, to remain flexible and lightweight in structure. As the position of the guide is preferably rigidized and maintained, the endoscope may then be advanced over the guide in a monorail or "piggy-back" fashion so that the flexible proximal portion follows the curve held by the guide until the endoscope reaches the next point of curvature.

In some variations, the process of alternately advancing the guide and the endoscope may be repeated to advance the entire endoscope through the colon while the guide may be alternatively rigidized and relaxed while being advanced distally. While the endoscope is advanced through the colon, the physician or surgeon may stop the advancement to examine various areas along the colon wall using, e.g., an imaging bundle located at the distal end of the endoscope. During such examinations, the guide may be temporarily withdrawn from the endoscope to allow for the insertion of other tools through the guide channel if there is no separate channel defined within the endoscope for the guide. The guide may also be withdrawn through the instrument to any location within the body of the endoscope. In other words, the guide may be withdrawn partially or removed entirely from the endoscope at any time, if desired, because there are no constraints which may limit the travel of the guide through the body of the endoscope. After a procedure has been completed on the colon wall, the tool may be withdrawn from the guide channel and the guide may be reintroduced into the endoscope so that the endoscope may optionally be advanced once again into the colon.

A further variation on advancing the endoscope may use multiple guides which are alternately rigidized while being advanced distally along a path. Although multiple guides may be used, two guides are preferably utilized. As the endoscopic device approaches a curvature, a first guide may be advanced in a relaxed and flexible state towards the steerable distal end of the device. While being advanced, the first guide preferably conforms to the shape defined by the distal end and the first guide may be subsequently rigidized to maintain this shape. The device may then be advanced further distally along the pathway while riding over the rigidized first guide.

After the device has been advanced to its new position, a second guide may also be advanced distally in its relaxed state through the device up to the distal end while the first guide is maintained in its rigidized state. The second guide may then conform to the new shape defined by the distal end of the device and become rigidized to maintain this new shape. At this point, the first guide is also preferably maintained in its rigid state until the distal end of the device has been advanced further distally. The first guide may then be relaxed and advanced while the rigidity of the second guide provides the strength for advancing the guide. This procedure may be repeated as necessary for negotiating the pathway.

To withdraw the endoscope from within the colon, the procedure above may be reversed such that the withdrawal minimally contacts the walls of the colon. Alternatively, the guide may simply be removed from the endoscope while leaving the endoscope within the colon. Alternatively, the guide may be left inside the endoscope in the relaxed mode. The endoscope may then be simply withdrawn by pulling the proximal portion to remove the device. This method may rub or contact the endoscope upon the walls of the colon, but any impingement would be minimal.

The selectively steerable distal portion can be selectively steered or bent up to a full 180° bend in any direction. A fiberoptic imaging bundle and one or more illumination fibers may extend through the body from the proximal portion to the distal portion. The illumination fibers are preferably in communication with a light source, i.e., conventional light sources, which may be positioned at some external location, or other sources such as LEDs. Alternatively, the endoscope may be configured as a video endoscope with a miniaturized video camera, such as a CCD camera, positioned at the distal portion of the endoscope body. The video camera may be used in combination with the illumination fibers. Optionally, the body of the endoscope may also include one or two access lumens that may optionally be used for insufflation or irrigation, air and water channels, and vacuum channels, etc. Generally, the body of the endoscope is highly flexible so that it is able to bend around small diameter curves without buckling or kinking while maintaining the various channels intact. The endoscope can be made in a variety of other sizes and configurations for other medical and industrial applications.

In some variations the endoscope may optionally include a suction device that can withdraw air or other gases, e.g. gases used for insufflating the interior of a colon. In the example of insufflating a colon, the insufflated gas may be trapped within regions of the colon due to the sacculation and movement of the colon walls. To facilitate removal of these gases, the suction device may be utilized to withdraw these trapped gases as the endoscope is advanced or withdrawn through the colon.

The suction device may comprise a suction tube positioned within the endoscope and connected to a suction port defined along the endoscope outer surface at a location proximal of the distal tip. The suction port can apply suction at some distance from the tip of the endoscope so that the suction does not interfere with insufflation or other activities at the distal end of the endoscope. In one variation, the suction port is located in the distal half of the endoscope, approximately one-quarter down the length of the insertable portion of the endoscope, e.g., 40 to 50 cm from the steerable tip. Some variations may apply suction continuously, while others allow the user to selectively control application of the suction.

The optional controllable portion is composed of at least one segment and preferably several segments which may be controllable via a computer and/or controller located at a distance from the endoscope. In one variation, approximately half of the length of the endoscope is comprised of controllable segments. Each of the segments preferably have an actuator mechanically connecting adjacent segments to allow for the controlled motion of the segments in space. The actuators driving the segments may include a variety of different types of mechanisms, e.g., pneumatic, vacuum, hydraulic, electromechanical motors, drive shafts, etc. If a mechanism such as a flexible drive shaft were utilized, the power for actuating the segments would preferably be developed by a generator located at a distance from the segments, i.e., outside of a patient during use, and in electrical and mechanical communication with the drive shaft. Alternatively, segments could be actuated by push-pull wires or tendons, e.g. Bowden cables, that bend segments by distributing force across a segment, as described in "Tendon-Driven Endoscope and Methods of Insertion" filed Aug. 27, 2002 (Ser. No. 10/229,557), which is incorporated in its entirety by reference.

A proximal portion comprises the rest of the endoscope and preferably a majority of the overall length of the device. The proximal portion is preferably a flexible tubing member that may conform to an infinite variety of shapes. It may also be covered by a polymeric covering optionally extendable over the controllable portion and the steerable distal portion as well to provide a smooth transition between the controllable segments and the flexible tubing of the proximal portion. The controllable portion may be optionally omitted from the endoscope. A more detailed description on the construction and operation of the segments may be found in U.S. patent application Ser. No. 09/969,927 entitled "Steerable Segmented Endoscope and Method of Insertion" filed Oct. 2, 2001, which has been incorporated by reference in its entirety.

A proximal handle may be attached to the proximal end of the proximal portion and may include imaging devices connected to the fiberoptic imaging bundle for direct viewing and/or for connection to a video camera or a recording device. The handle may be connected to other devices, e.g., illumination sources and one or several luer lock fittings for connection to various instrument channels. The handle may also be connected to a steering control mechanism for controlling the steerable distal portion. The handle may optionally have the steering control mechanism integrated directly into the handle, e.g., in the form of a joystick, conventional disk controller using dials or wheels, etc. An axial motion transducer may also be provided for measuring the axial motion, i.e., the depth change, of the endoscope body as it is advanced and withdrawn. The axial motion transducer can be made in many possible configurations. As the body of the endoscope slides through the transducer, it may produce a signal indicative of the axial position of the endoscope body with respect to the fixed point of reference. The transducer may use various methods for measuring the axial position of the endoscope body.

The guide is generally used to impart a desired curvature initially defined by the steerable portion and/or by the optional controllable portion to the passive proximal portion when the endoscope is advanced. If held or advanced into the steerable portion, the guide is preferably advanced to or near the distal tip of the portion. It is also used to impart some column strength to the proximal portion in order to maintain its shape and to prevent any buckling when axially loaded. Preferably, the guide is slidably disposed within the length of the endoscope body and may freely slide entirely through the passive proximal portion, through the controllable portion, and the steerable distal portion. The extent to which the guide may traverse through the endoscope body may be varied and adjusted according to the application, as described above. Furthermore, the proximal end of the guide may be routed through a separate channel to a guide controller which may be used to control the advancement and/or withdrawal of the guide and which may also be used to selectively control the rigidity of the guide as controlled by the physician.

The structure of the guide may be varied according to the desired application. The following descriptions of the guide are presented as possible variations and are not intended to be limiting in their structure. For instance, the guide may be comprised of two coaxially positioned tubes separated by a gap. Once the guide has been placed and has assumed the desirable shape or curve, a vacuum force may be applied to draw out the air within the gap, thereby radially deforming one or both tubes such that they come into contact with one another and lock their relative positions.

Another variation on the guide is one which is rigidizable by a tensioning member. Such a guide may be comprised of a series of individual segments which are rotatably interlocked with one another in series. Each segment may further define a common channel through which a tensioning member may be positioned while being held between a proximal and a distal segment. During use, the tensioning member may be slackened or loosened enough such that the guide becomes flexible enough to assume a shape or curve defined by the endoscope. When the guide is desirably situated and has assumed a desired shape, the tensioning member may then be tensioned, thereby drawing each segment tightly against one another to hold the desired shape.

Another variation may use a guide which is comprised of interlocking ball-and-socket type joints which are gasketed at their interfaces. Such a design may utilize a vacuum pump to selectively tighten and relax the individual segments against one another. Other variations may include alternating cupped segments and ball segments, a series of collinear sleeve-hemisphere segments, as well as other designs which may interfit with one another in series. Such a guide may be tightened and relaxed either by tensioning members or vacuum forces.

A further variation on the guide is a coaxially aligned stiffening member. This assembly may include a first subassembly comprising a number of collinearly nested segments which may be held by a tensioning member passing through each segment. The first subassembly may be rigidized from a flexible or flaccid state by pulling on this tensioning member. A second subassembly may comprise a number of annular segments also collinearly held relative to one another with one or more tensioning members passing through each annular segment. The second subassembly preferably defines a central area in which the first nested subassembly may be situated coaxially within the second subassembly. The first subassembly is preferably slidably disposed relative to the second subassembly thereby allowing each subassembly to be alternately advanced in a flexible state and alternately rigidized to allow the other subassembly to be advanced. This design presents a small cross-section relative to the endoscope or device through which it may be advanced.

BRIEF DESCRIPTION OF THE DRAWINGS

FIG. 3A shows a side view of an endoscopic device variation with the outer layers removed to reveal a guiding apparatus disposed within.

FIGS. 4A to 4C show cross-sectional views of various examples of guiding apparatus which may be used to guide an endoscope.

DETAILED DESCRIPTION OF THE INVENTION

Figure 1:
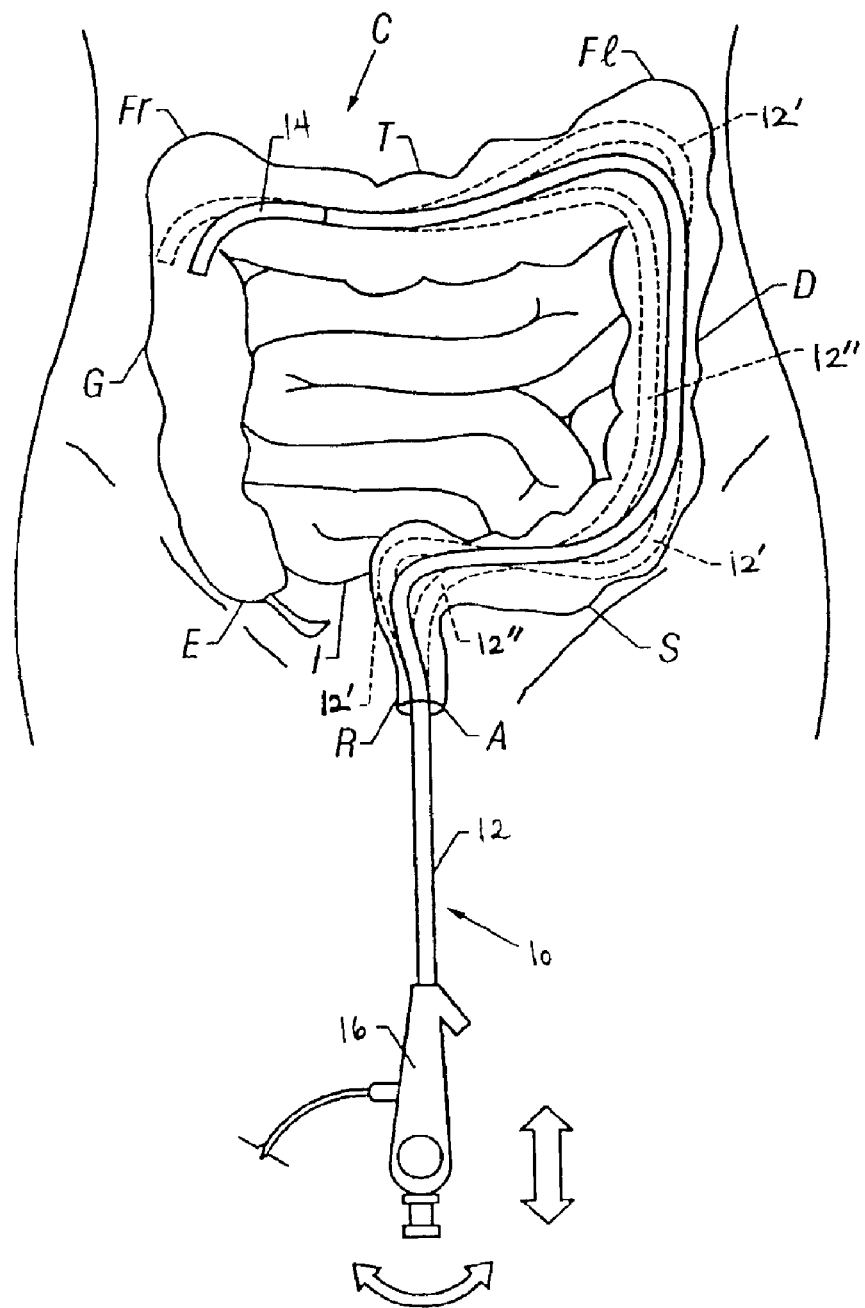
FIG. 1 shows a representation of a conventional endoscope in use.

FIG. 1 shows a prior art colonoscope 10 being employed for a colonoscopic examination of a patient's colon C. The colonoscope 10 has a proximal handle 16 and an elongate body 12 with a steerable distal portion 14. The body 12 of the colonoscope 10 has been lubricated and inserted into the colon C via the patient's anus A. Utilizing the steerable distal portion 14 for guidance, the body 12 of the colonoscope 10 has been maneuvered through several turns in the patient's colon C to the ascending colon G. Typically, this involves a considerable amount of manipulation by pushing, pulling and rotating the colonoscope 10 from the proximal end to advance it through the turns of the colon C. After the steerable distal portion 14 has passed, the wall of the colon C maintains the curve in the flexible body 12 of the colonoscope 10 as it is advanced. Friction develops along the body 12 of the colonoscope 10 as it is inserted, particularly at each turn in the colon C. Because of the friction, when the user attempts to advance the colonoscope 10, the body 12' tends to move outward at each curve, pushing against the wall of the colon C, which exacerbates the problem by increasing the friction and making it more difficult to advance the colonoscope 10. On the other hand, when the colonoscope 10 is withdrawn, the body 12" tends to move inward at each curve taking up the slack that developed when the colonoscope 10 was advanced. When the patient's colon C is extremely tortuous, the distal end of the body 12 becomes unresponsive to the user's manipulations, and eventually it may become impossible to advance the colonoscope 10 any farther. In addition to the difficulty that it presents to the user, tortuosity of the patient's colon also increases the risk of complications, such as intestinal perforation.

Figure 2A:
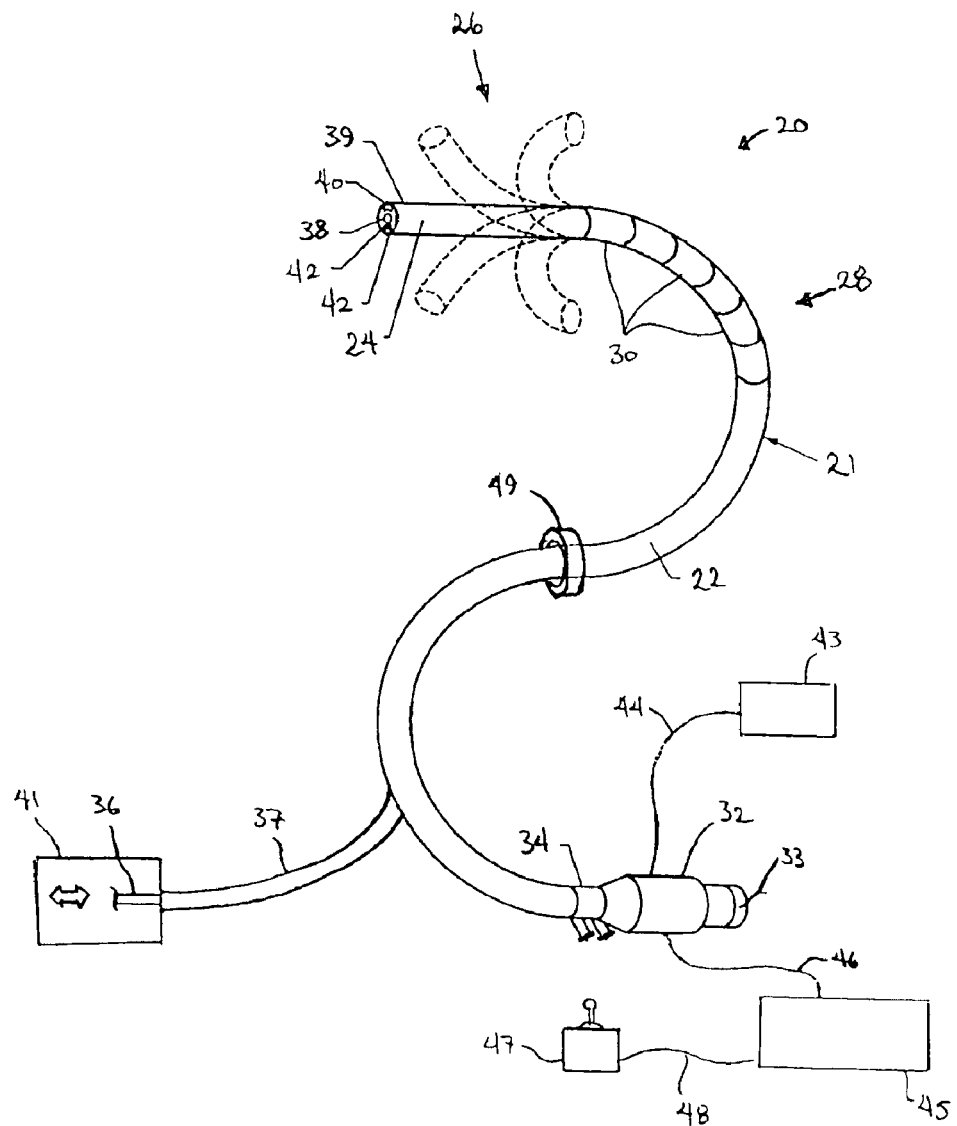
FIG. 2A shows a variation of an endoscopic device of the present invention.

FIG. 2A shows a variation of the steerable endoscope 20 of the present invention. The endoscope 20 has an elongate body 21 with a manually or selectively steerable distal portion 24, an automatically controlled portion 28, which may be optionally omitted from the device, a flexible and passively manipulated proximal portion 22, and an externally controlled and manipulatable tracking rod or guide 36 which may be slidably positioned within the endoscope 20.

The selectively steerable distal portion 24 can be selectively steered or bent up to a full 180° bend in any direction 26, as shown in the figure. A fiberoptic imaging bundle 40 and one or more illumination fibers 42 may extend through the body 21 from the proximal portion 22 to the distal portion 24. Alternatively, the endoscope 20 may be configured as a video endoscope with a miniaturized video camera, such as a CCD camera, positioned at the distal portion 24 of the endoscope body 21. The images from the video camera can be transmitted to a video monitor by a transmission cable or by wireless transmission where images may be viewed in real-time or recorded by a recording device onto analog recording medium, e.g., magnetic tape, or digital recording medium, e.g., compact disc, digital tape, etc. Optionally, the body 21 of the endoscope 20 may include one or two access lumens 38 that may optionally be used for illumination fibers for providing a light source, insufflation or irrigation, air and water channels, and vacuum channels. Generally, the body 21 of the endoscope 20 is highly flexible so that it is able to bend around small diameter curves without buckling or kinking while maintaining the various channels intact. When configured for use as a colonoscope, the body 21 of the endoscope 20 may range typically from 135 to 185 cm in length and about 13–21 mm in diameter. The endoscope 20 can be made in a variety of other sizes and configurations for other medical and industrial applications.

The optional controllable portion 28 is composed of at least one segment 30, and preferably several segments 30, which may be controllable via a computer and/or controller located at a distance from the endoscope 20. Each of the segments 30 preferably has an actuator mechanically connecting adjacent segments 30 to allow for the controlled motion of the segments 30 in space. The actuators driving the segments 30 may include a variety of different types of mechanisms, e.g., pneumatic, hydraulic, electromechanical motors, "off board" powered drive shafts, tendons, etc. A proximal portion 22 comprises the rest of the endoscope 20 and preferably a majority of the overall length of the device 20. Proximal portion 20 is preferably a flexible tubing member which may conform to an infinite variety of shapes. It may also be covered by a polymeric covering 39 optionally extendable over controllable portion 28 and steerable distal portion 24 as well to provide a smooth transition between the controllable segments 30 and the flexible tubing of proximal portion 22. The proximal portion 22 may be made from a variety of materials such as thermoset and thermoplastic polymers which are used for fabricating the tubing of conventional endoscopes.

A proximal handle 32 may be attached to the proximal end of the proximal portion 22. The handle 32 may include an ocular 33 connected to the fiberoptic imaging bundle 42 for direct viewing. The handle 32 may otherwise have a connector for connection to a video camera, e.g., a CCD camera, or a recording device. The handle 32 may be connected to an illumination source 43 by an illumination cable 44 that is connected to or continuous with the illumination fibers 42. One or several luer lock fittings 34 may be located on the handle 32 and connected to the various instrument channels.

The handle 32 is connected to an electronic motion controller 45 by way of a controller cable 46. A steering control 47 may be connected to the electronic motion controller 45 by way of a second cable 48 or it may optionally be connected directly to the handle 32. Alternatively, the handle may have the steering control mechanism integrated directly into the handle, e.g., in the form of a joystick, conventional disk controllers such as dials or wheels, etc. The steering control 47 allows the user to selectively steer or bend the selectively steerable distal portion 26 of the body 21 in the desired direction. The steering control 47 may be a joystick controller as shown, or other known steering control mechanism. The electronic motion controller 45 controls the motion of the automatically controlled proximal portion 28 of the body 21. The electronic motion controller 45 may be implemented using a motion control program running on a microcomputer or using an application-specific motion controller. Alternatively, the electronic motion controller 45 may be implemented using, e.g., a neural network controller.

An axial motion transducer 49 may be provided for measuring the axial motion, i.e., the depth change, of the endoscope body 21 as it is advanced and withdrawn. The axial motion transducer 49 can be made in many possible configurations. For example, the axial motion transducer 49 in FIG. 2A is configured as a ring 49 that may surround the body 21 of the endoscope 20. The axial motion transducer 49 is preferably attached to a fixed point of reference, such as the surgical table or the insertion point for the endoscope 20 on the patient's body. As the body 21 of the endoscope 20 slides through the axial motion transducer 49, it produces a signal indicative of the axial position of the endoscope body 21 with respect to the fixed point of reference and sends a signal to the electronic motion controller 45 by telemetry or by a cable. The axial motion transducer 49 may use optical, electronic or mechanical methods to measure the axial position of the endoscope body 21.

Similarly, when the endoscope body 21 is withdrawn proximally, each time the endoscope body 21 is moved proximally by one unit, each section in the automatically controlled proximal portion 28 is signaled to assume the shape of the section that previously occupied the space that it is now in. The curve propagates distally along the length of the automatically controlled proximal portion 28 of the endoscope body 21, and the shaped curve appears to be fixed in space, as the endoscope body 21 withdraws proximally. Alternatively, the segments of controlled portion 28 could be made to become flaccid and the withdrawal would then be passive.

Whenever the endoscope body 21 is advanced or withdrawn, the axial motion transducer 49 detects the change in position and the electronic motion controller 45 propagates the selected curves proximally or distally along the controllable portion 28 of the endoscope body 21 to maintain the curves in a spatially fixed position. The axial motion transducer 49 also allows for the incrementing of a current depth within the colon C by the measured change in depth. This allows the endoscope body 21 to be guided through tortuous curves without putting unnecessary force on the wall of the colon C. As mentioned above, such a segmented body 30 within the controllable portion 28 may be actuated by a variety of methods. One method involves the use of electromechanical motors which may be individually mounted on each segment 30 to move the segments 30 relative to one another. Each segment 30 preferably defines at least one lumen running through it to provide an access channel through which wires, optical fibers, air and/or water channels, various endoscopic tools, or any variety of devices and wires may be routed through.

A more detailed description on the construction and operation of the segments may be found in U.S. patent application Ser. No. 09/969,927 entitled "Steerable Segmented Endoscope and Method of Insertion" filed Oct. 2, 2001, which has been incorporated by reference in its entirety.

The guide 36 is generally used to impart a desired curvature initially defined by the steerable distal portion 24 and/or by the optional controllable portion 28 to the passive proximal portion 22 when the endoscope 20 is advanced. If the guide 36 is advanced into the steerable distal portion 24, guide 36 is preferably advanced to or near the distal tip of the portion 24. The guide 36 may also be used partly to impart some column strength to the proximal portion 22 in order to maintain its shape and to prevent any buckling when axially loaded, such as when the endoscope 20 is advanced through a patient's colon. Construction of an endoscope 20 with the use of the guide 36 not only simplifies the control systems involved but it also represents a cost efficient device. Operation of the endoscope 20 with guide 36 will be discussed in detail below.

Preferably, the guide 36 is slidably disposed within the length of the endoscope body 21 and may freely slide entirely through the passive proximal portion 22, through the optional controllable portion 28, if utilized in the endoscope, and the steerable distal portion 24. Guide 36 may also be withdrawn through the instrument to any location within the body of endoscope 20. Moreover, guide 36 may be removed entirely from endoscope 20, if desired e.g., to accommodate additional working tools. In other words, there are preferably no constraints which may limit the travel of guide 36 within the body of endoscope 20.

Guide 36 may be advanced through proximal handle 32; alternatively, guide 36 may also be routed through a separate channel 37 dedicated to the guide 36. Channel 37 is preferably attached to endoscope 20 near a proximal end of the instrument, such as a location off the proximal portion 22, and leads to a guide controller 41 which may be used to advance and/or withdraw guide 36 through endoscope 20. Guide controller 41 may also be used to selectively rigidize and relax guide 36 during use within a patient. Having guide controller 41 and proximal handle 32 separated may allow for the ease of use for the physician manipulating the endoscope 20. To aid in advancing guide 36 through endoscope 20, a pulley mechanism may be affixed within the steerable distal portion 24 through which a pull wire may extend over to connect the distal end of the guide 36 to a location outside the endoscope 20 for manipulation by the physician.

To facilitate the movement of guide 36 through endoscope body 21, a lubricious covering or coating may be applied over at least a majority of the length of guide 36 or onto the inner surface of the lumen through which guide 36 traverse, or both. Such coverings may include various polymers and plastics, e.g., PTFE, etc., which may simply cover the guide 36 length or which may be heatshrunk, coated, or bonded onto guide 36, depending upon the material used. The extent to which guide 36 traverses through the endoscope body 21 may be varied and adjusted according to the application.

Figure 2B:
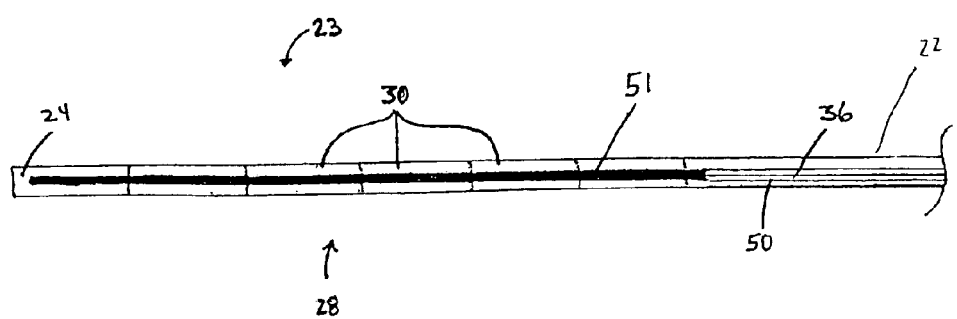
FIGS. 2B and 2C show side sectional views of another variation of the present invention.
Figure 2C:
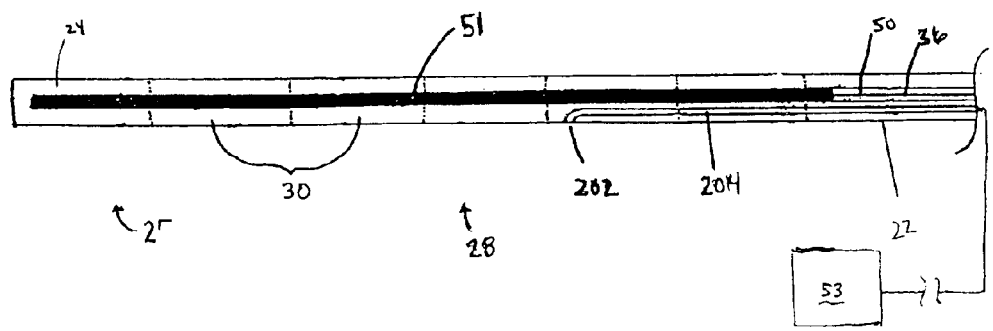

FIGS. 2B and 2C show sectional partial views of a variation of the endoscope that is capable of single-step use of the guide. In these variations, the axial length of the guide 51 is shorter than the insertable length of the endoscope 23. The endoscope body 21 includes a steerable distal tip 24 and a proximal controllable region 28 that is comprised of flexible segments 30. Approximately half of the length of the endoscope body may be composed of controllable segments 30, and the remaining proximal part of the endoscope is flexible passive portion 22. The length of the guide 51 is approximately half that of the endoscope body 23. Although the guide 51 is freely slidable within lumen 50 of the endoscope 23 in the variation shown, the guide 51 may be preloaded through the distal end of the endoscope 23 before insertion into the body. Alternatively, the guide 51 could be positioned as described above. The guide 51 can be rigidized and held in place by the tensioning wire 36. The combination of steerable distal tip 24, controllable proximal portion 28 and guide 51 in this variation of the invention simplifies the use of the rigidizable guide 51 because the guide 51 only has to be rigidized and locked into position once.

FIG. 2C shows another, slightly magnified, sectional view of the endoscope of FIG. 2B. This view illustrates an optional suction device 53, e.g., a negative pressure pump device, which may be fluidly connected to suction port 202 through suction tube 204. Suction device 53 is preferably located externally of the patient during use. Because insufflated air or gas may be trapped within regions of the colon due to the sacculation and movement of the colon walls, the suction device 53 may be used to facilitate removal of these gases as the endoscope is advanced or withdrawn through the colon. The suction port 202 shown is preferably located at some point proximal of distal end 24, e.g., approximately one quarter of the length of the endoscope body 23. This suction port can be located virtually anywhere along the length of the endoscope, but it is preferably located such that it does not interfere with the insufflation process at or near the distal tip.

FIG. 3A shows an isometric view of a length of the endoscope 20, in this example part of the proximal portion 22, with a section of the endoscope body 20 removed for clarity. As seen, a representative illustration of the guide 36 may be seen disposed within guide channel or lumen 50 within the proximal portion 22. Lumen 50 may be an existing working channel, i.e., an access channel for other tools, or it may be a designated channel for guide 36 depending upon the desired application. Guide 36 may be inserted within guide channel 50 through the endoscope handle 32 and pushed proximally through the remainder of the device, as seen in FIG. 2A; or preferably, it may be pushed proximally or pulled distally, as necessary, through a separate guide controller 41, as discussed above. Although guide 36 is shown in this variation as being slidably disposed interiorly of endoscope body 20, it may also be disposed exteriorly of the body 20 to slide along a guide rail or exterior channel in other variations.

If guide 36 is located within a dedicated channel, such as lumen 50, the distal end of this channel is preferably closed or blocked at some distal location, e.g., within steerable distal portion 24 or within optional controllable portion 28, to prevent the influx of bodily fluids within lumen 50. Because an enclosed lumen 50 would further prevent contact of bodily fluids with guide 36, the amount of cleaning or sterilization of guide 36 is reduced.

Figure 3C:
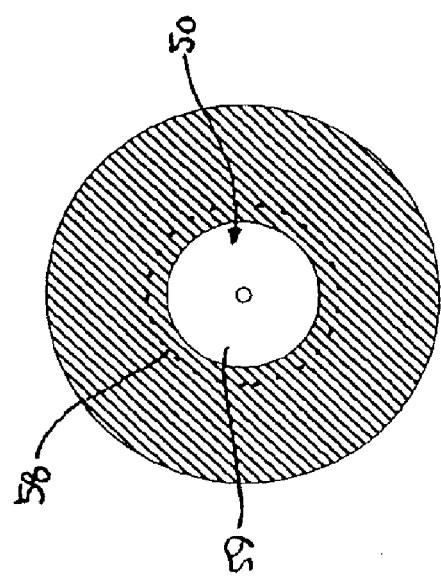
FIGS. 3B and 3C show cross-sectional views of various examples for obstructing the guide lumen of the endoscope.
Figure 3B:
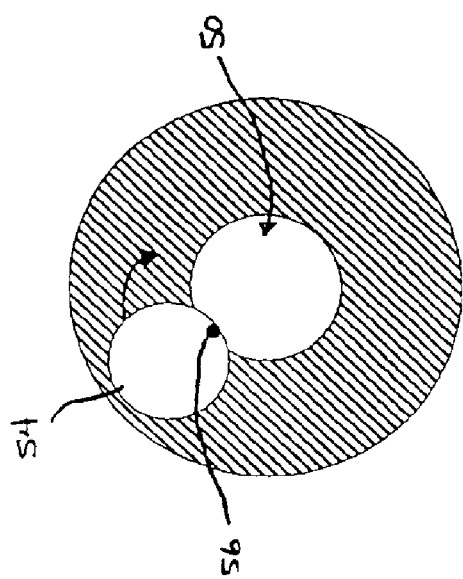

If lumen 50 were left as an open channel, additional sterilization or cleaning and disinfecting of guide 36 and lumen 50 may be necessary. Alternatively, lumen 50 may be left as an open channel but configured to have optional closing mechanisms, as shown in the examples of FIGS. 3B and 3C, taken from FIG. 3A. FIG. 3B shows an end view of a trap or door 54 which is held within the body of the instrument and which may be rotated about a pivot 56 in the direction of the arrow to close access to lumen 50. Trap 54 may be closed during insertion of the instrument within a patient and then optionally opened to allow for working tools to be inserted therethrough. FIG. 3C shows another example where lumen 50 may be obstructed by an inflatable balloon 59 which may selectively expand to completely obstruct the passageway. Balloon 59 may be made of conventional materials and may be held within a compartment or step 58 such that lumen 50 is unobstructed when balloon 59 is deflated. These examples merely present variations and are not meant to limit the scope of the invention. Alternative designs and variations are intended to be within the scope of the present invention.

FIGS. 4A to 4C show variations on possible cross-sections 4A–4A, 4B–4B, and 4C–4C, respectively, taken from FIG. 3A. FIG. 4A shows a simplified cross-section 22' of a guide 36 having a circular diameter slidably disposed within proximal portion 22. As seen, guide 36 may be slidably positioned within channel 50', which may also be used as a working channel upon removal of guide 36 during, e.g., a colonoscopy procedure, for providing access for various instruments or tools to a treatment site. FIG. 4B shows another possible variation in cross-section 22" where guide 36 is positioned within channel 50". The variation of the proximal portion in cross-section 22" may include a number of access lumens 52 optionally formed within the body of the device 20. These lumens 52 may run through the length of device 20 and may be used for various applications, e.g., illumination fibers, laparoscopic tools, etc. Although three lumens 52 are shown in the figure, any number of channels as practically possible may be utilized depending upon the application at hand. FIG. 4C shows another variation in cross-section 22'". In this variation, guide 36' may be formed into a semi-circular or elliptical shape to slide within a similarly shaped channel 50'". In this example, proximal portion 22'" also includes a working channel 52' which may be shaped accordingly to fit within the body 22'" along with channel 50'" to maintain a working channel without having to remove guide 36'. In any of the above examples, the working or guide channels are preferably integral structures within the body of endoscope 20. Having an integral structure eliminates the need for a separate lumened structure, e.g., a separate sheath, through which guide 36 or any other tools may be inserted. Another variation utilizing multiple channels and multiple guides will be described in further detail below. These variations are not intended to be limiting but are merely presented as possible variations. Other structures and variations thereof may be recognized by one of skill in the art and are intended to be within the scope of the claims below.

Figure 5A:
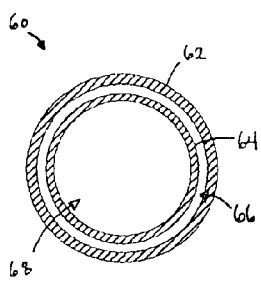
FIGS. 5A and 5B show the cross-sectioned end and side views, respectively, of a guiding apparatus with a vacuum-actuated rigidizing variation.
Figure 5B:
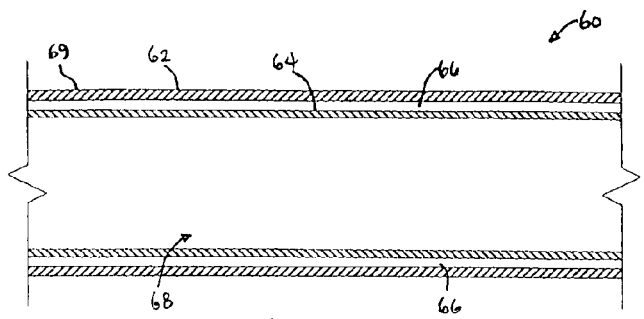

The structure of the guide may be varied according to the desired application. The following description on the guide is presented as possible variations and are not intended to be limiting in their structure. FIGS. 5A and 5B show cross-sectioned end and side views, respectively, of a guiding apparatus variation which is rigidizable by a vacuum force applied within the guide. It is preferable that the guide is selectively rigidizable, i.e., when the guide assumes a shape or curve in a flexible state, the guide may be rigidized to hold that shape or curve for a predetermined period of time. Although the endoscope structure of the present invention may utilize a guide which remains in a relatively flexible shape, it is preferable to have the guide be selectively rigidizable.

Guide 60 may be comprised of two coaxially positioned tubes, outer tube 62 and inner tube 64, which are separated by a gap 66 between the two tubes. Inner tube 64 may define an access lumen 68 throughout the length of the tube to provide a channel for additional tools or other access devices. Both tubes 62, 64 are preferably flexible enough to be bent over a wide range of angles and may be made from a variety of materials such as polymers and plastics. They are also preferably flexible enough such that either the outer tube 62, inner tube 64, or both tubes are radially deformable. Once guide 60 has been placed and has assumed the desirable shape or curve, a vacuum force may be applied to draw out the air within gap 66. This vacuum force may radially deform inner tube 64 and bring it into contact with the inner surface of outer tube 62 if inner tube 64 is made to be relatively more flexible than outer tube 62. Alternatively, if outer tube 62 is made to be relatively more flexible than inner tube 64, outer tube 62 may be brought into contact with the outer surface of inner tube 64.

In another variation, tubes 62, 64 may both be made to be flexible such that they are drawn towards one another. In yet another variation, which may be less preferable, a positive force of air pressure or a liquid, e.g., water or saline, may be pumped into access lumen 68. The positive pressure from the gas or liquid may force the walls of inner tube 64 radially into contact with the inner surface of outer tube 62. In any of these variations, contact between the two tubular surfaces will lock the tubes 62, 64 together by frictional force and make them less flexible. An elastomeric outer covering 69, or similar material, may optionally be placed upon the outer surface of outer tube 62 to provide a lubricious surface to facilitate the movement of guide 60 within the endoscopic device. An example of a device similar to guide 60 is discussed in further detail in U.S. Pat. No. 5,337,733, which has been incorporated herein by reference in its entirety.

Figure 6A:
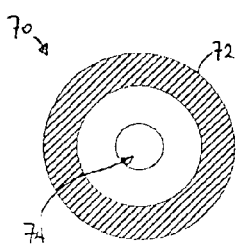
FIGS. 6A and 6B show the cross-sectioned end and side views, respectively, of a guiding apparatus with a tensioning or pre-tensioned element for rigidizing the guide.
Figure 6B:
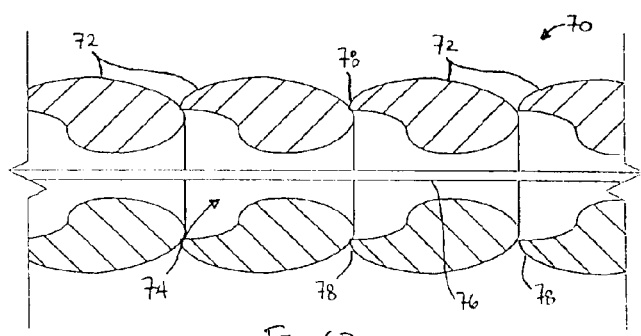

Another variation on the guide is shown in FIGS. 6A and 6B which show cross-sectioned end and side views, respectively, of a guiding apparatus variation 70 which is rigidizable by a tensioning member 76. Tensioned guide 70 is shown comprised of a series of individual segments 72 which are rotatably interlocked with one another in series. Each segment 72 may contact an adjoining segment 72 along a contacting lip 78. Each segment 72 may further define a channel therethrough which, collectively along with the other segments 72, form a common channel 74 throughout a majority of the length of guide 70. Segments 72 may be comprised of a variety of materials suitable for sustaining compression forces, e.g., stainless steel, thermoplastic polymers, plastics, etc.

Proximal and distal segments of guide 70 may hold respective ends of, tensioning member 76, which is preferably disposed within common channel 74 through guide 70. Tensioning member 76 may be connected to a tensioning housing located externally of a patient. During use when the guide is advanced distally through an endoscope of the present invention, tensioning member 76 is preferably slackened or loosened enough such that guide 70 is flexible enough to assume a shape or curve defined by the endoscope. When guide 70 is desirably situated and has assumed a desired shape, tensioning member 76 may be tensioned. This tightening or tensioning of member 76 will draw each segment 72 tightly against one another along each respective contacting lip 78 such that the guide 70 becomes rigid in assuming the desired shape. A lubricious covering, e.g., elastomers, etc., may be optionally placed over at least a majority of guide 70 to facilitate movement of the guide 70 relative to the endoscopic device. A similar concept and design is discussed in further detail in U.S. Pat. No. 5,624,381, which has been incorporated herein by reference in its entirety.

Figure 7A:
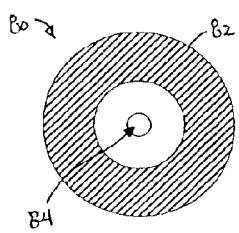
FIGS. 7A and 7B show the cross-sectioned end and side views, respectively, of a guiding apparatus with a segmented vacuum-actuated rigidizing variation.
Figure 7B:
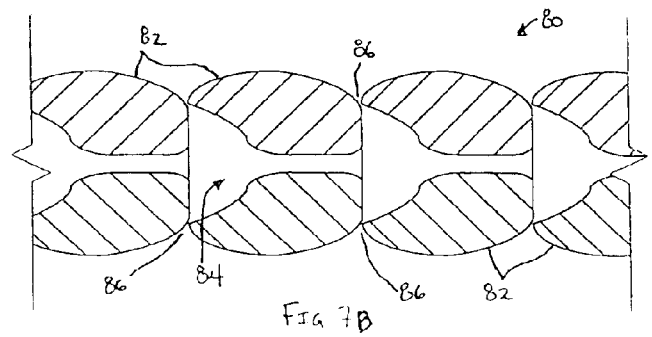

FIGS. 7A and 7B show cross-sectioned end and side views, respectively, of a guiding apparatus variation 80 which is rigidizable by a vacuum force which interlocks individual segments 82. Each segment 82 may be adjoined with adjacent segments by interlocking ball-and-socket type joints which are preferably gasketed at the interfaces 86 of each connection. Within each segment 82, with the exception of the distal segment, may be defined a channel which is narrowed at one end and flared at the opposite end. Collectively when the segments 82 are adjoined into the structure of guide 80, each of the individual channels form a common channel 84 which extends through at least a majority of the segments 82 along the length of guide 80. At the proximal end of guide 80 a vacuum pump, which is preferably located externally of the patient, is fluidly connected to common channel 84. In use, once guide 80 is manipulated in its flexible state within the endoscope to assume the desired shape or curve, ambient pressure may exist within common channel 84. When the rigid shape of guide 80 is desired, the pump may then be used to create a negative pressure within common channel 84 and this negative pressure draws each segment 82 into tight contact with one another to maintain the desired shape. When the vacuum force is released, each segment 82 would also be released and would thereby allow the guide 80 to be in its flexible state for advancement or withdrawal. Guide 80 may further be surrounded by an elastomeric or lubricious covering to aid in the advancement or withdrawal of the guide 80 within the endoscopic device.

Figure 8A:
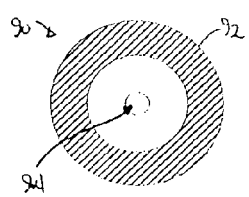
FIGS. 8A and 8B show the cross-sectioned end and side views, respectively, of a guiding apparatus with interconnecting jointed segments for rigidizing the guide.
Figure 8B:
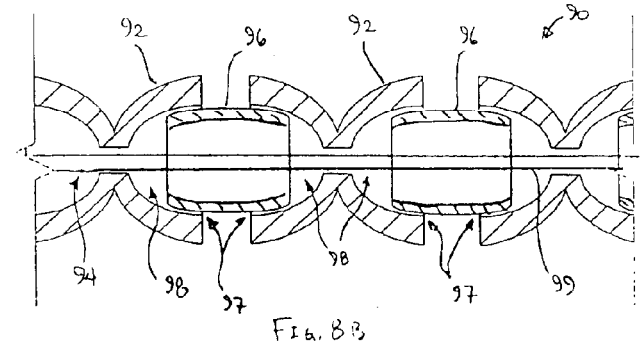

FIGS. 8A and 8B show cross-sectioned end and side views, respectively, of yet another guiding apparatus variation 90 which is optionally rigidizable by either a vacuum force or a tensioning member which interlocks individual segments 92. Segment 92 may be in the form of a segmented design with two opposed cups having a common channel 94 defined therethrough. Between each segment 92 are ball segments 96 which interfits along a contact rim or area 97 within each adjacent segment 92. Ball segments 96 preferably contact adjacent cupped segments 96 within receiving channels 98 defined in each cup. When manipulated in its flexible state, guide 90 may be advanced or withdrawn or made to assume a desired shape or curve. When guide 90 is to be placed into its rigidized shape, a vacuum force or tensioning member 99 may be utilized in the guide 90 in similar manners as described above. Moreover, guide 90 may similarly be surrounded by an elastomeric or lubricious covering to aid in the advancement and withdrawal of the guide 90.

Figures 9A, 9B:
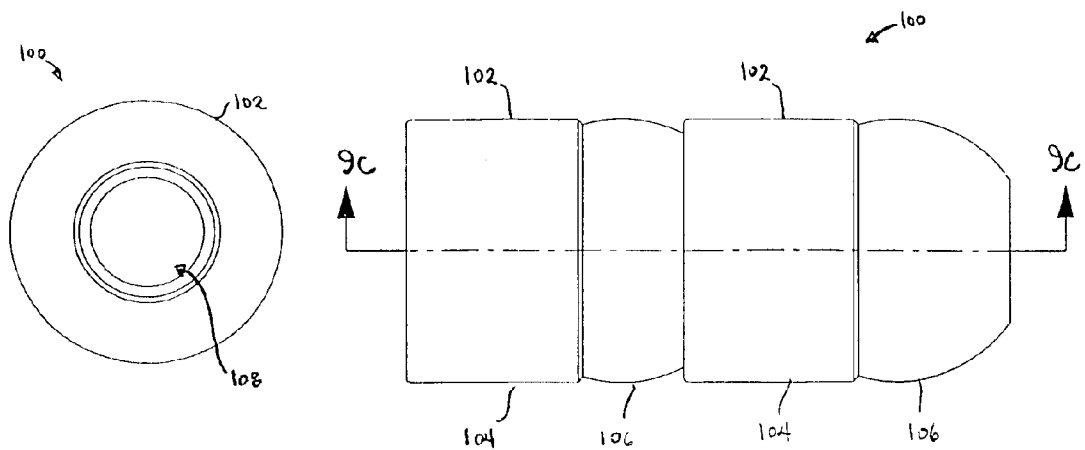
FIGS. 9A to 9C show end, side, and cross-sectioned views, respectively, of another variation on the guiding apparatus.
Figure 9C:
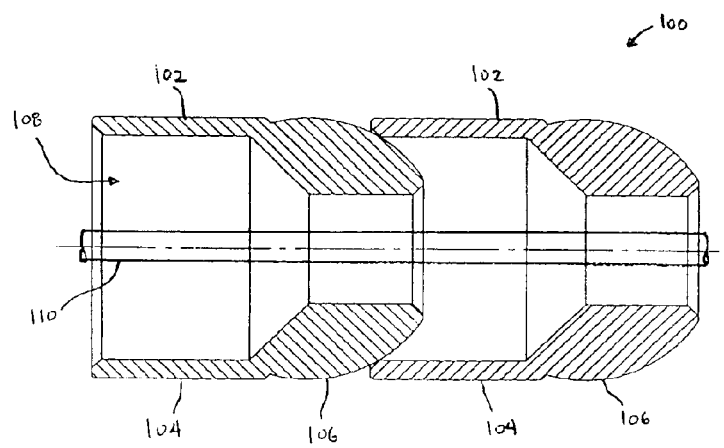

FIGS. 9A and 9B show representative end and side views, respectively, of another guiding apparatus variation 100. This variation 100 comprises individual segments 102 having a uniform sleeve section 104 in combination with an integrated curved or hemispherical section 106. Each segment 102 is collinearly aligned with one another with the sleeve section 104 receiving the curved section 106 of an adjacent segment 102, as shown in FIG. 9C, which is the cross-section of guide 100 from FIG. 9B. The adjacent segments 102 may rotate relative to one another over the sleeve-hemisphere interface while maintaining a common channel 108 through the guide 100. A tensioning member 110 may pass through channel 108 along the length of guide 100 for compressing the individual segments 102 against one another when the entire guide 100 is rigidized.

Figure 10:
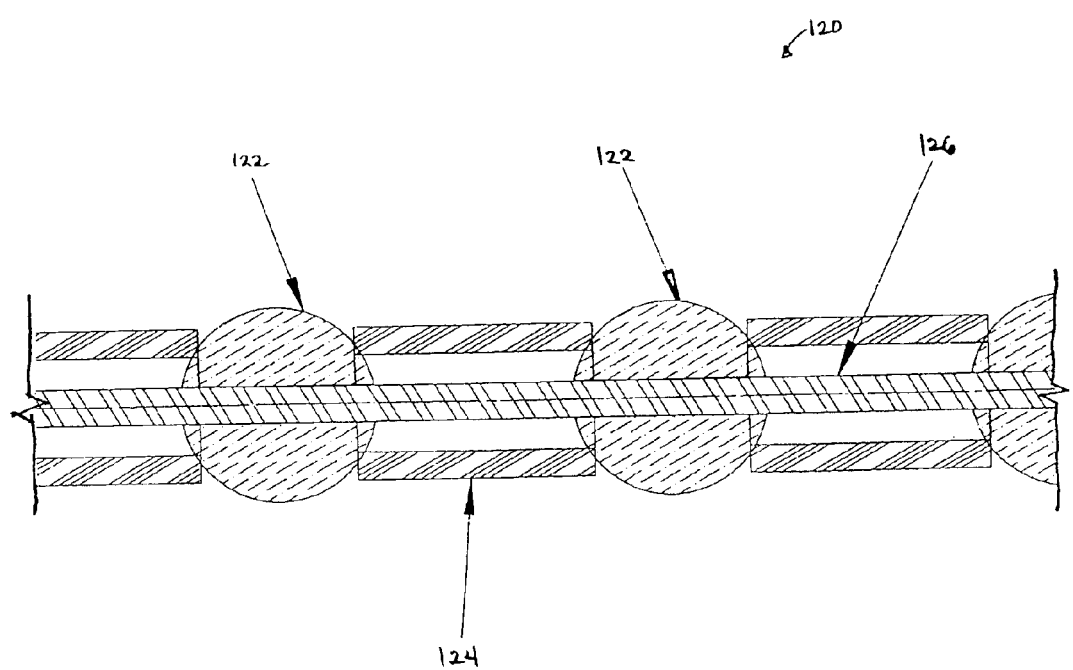
FIG. 10 shows the cross-sectioned side view of another variation on the guiding apparatus having alternating bead and sleeve segments.

FIG. 10 shows the cross-section of another variation 120 of the rigidizable guide apparatus. Representative segments are shown comprising spherical bead segments 122 alternating with sleeve segments 124. Each of the bead and sleeve segments 122, 124, respectively, may have a channel defined therethrough which allows for a tensioning member 126 to be run through the length of guide 120. The alternating segments allow for the rotation of the adjacent segments while the tensioning member 126 allows for the compression of the segments against one another when the guide 120 is to be rigidized in much the same manner as described above.

Figure 11A:
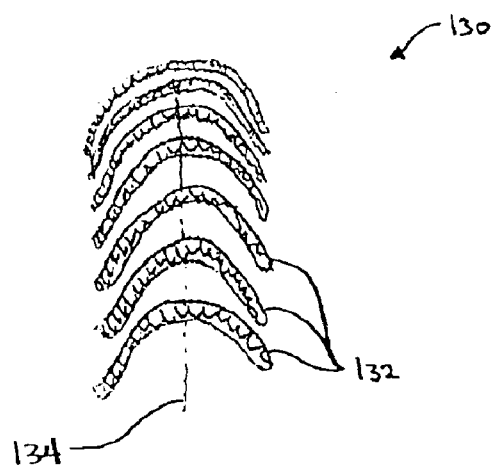
FIG. 11A shows a side view of a nested guiding apparatus which is part of a coaxial stiffening assembly.
Figure 11B:
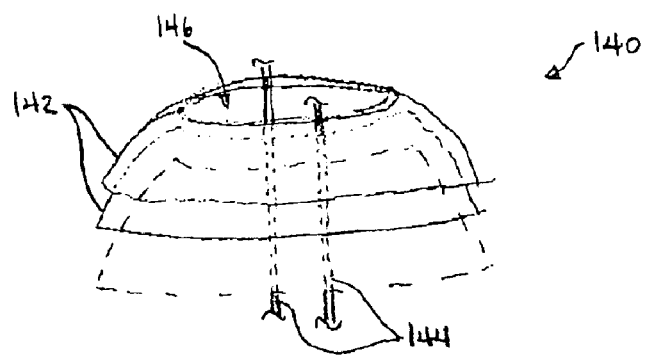
FIG. 11B shows a side view of an annular guiding apparatus which is also part of the coaxial stiffening assembly.
Figure 11C:
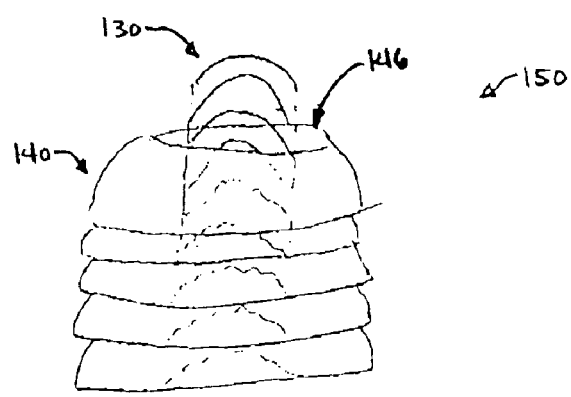
FIG. 11C shows the combination of the guides from FIGS. 11A and 11B.

An alternative variation on the rigidizable guide is illustrated in FIGS. 11A to 11C, which show a stiffening assembly having separate rigidizable coaxially positioned guides. FIG. 11A shows a representative number of nested segments 132 in nested stiffening assembly 130. Each nested segment 132 may be in a number of different configurations, e.g., ball socket joints, stacked ring-like segments, etc., with a tensioning member 134 passing through each of the segments 132. For use with nested assembly 130, an annular stiffening assembly 140 may be seen in FIG. 11B. Annular assembly 140, of which only a few representative segments are shown, are comprised in this variation of annular segments 142 which may be stacked or aligned one atop each other. At least one tensioning member 144, and preferably at least two, may be passed through each of the annular segments 142. A central area 146 is defined in each annular segment 142 such that nested stiffening assembly 130 may be slidingly placed within the central area 146 defined by the annular stiffening assembly 140. FIG. 11C shows the stiffening assembly 130 slidingly positioned within annular stiffening assembly 140 to form the coaxially aligned stiffening assembly 150. Use of coaxial assembly 150 will be described in further detail below.

Figure 12A:
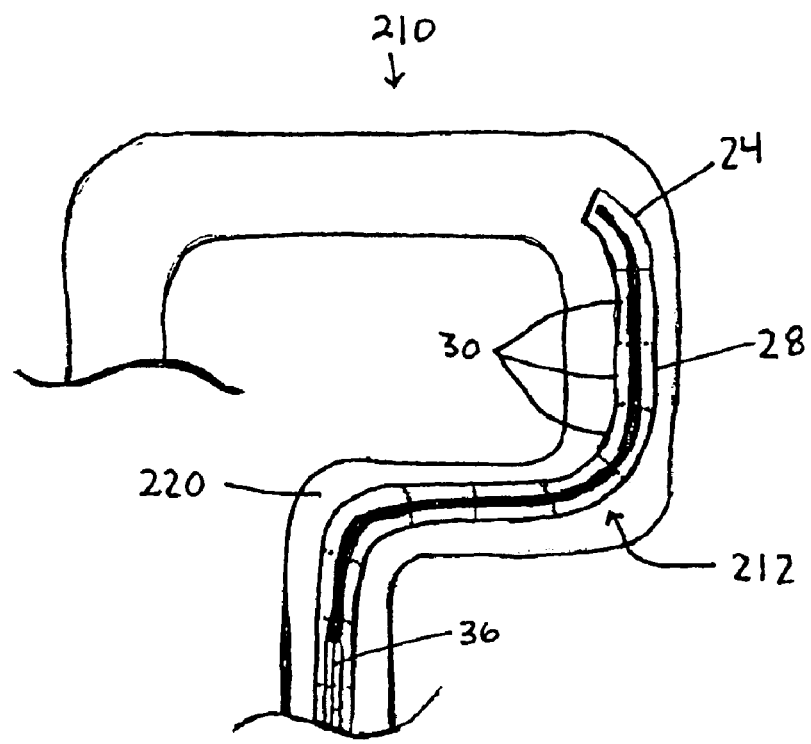
FIGS. 12A and 12B illustrate a representative example of advancing the endoscope along a tortuous pathway using a single rigidizing step.
Figure 12B:
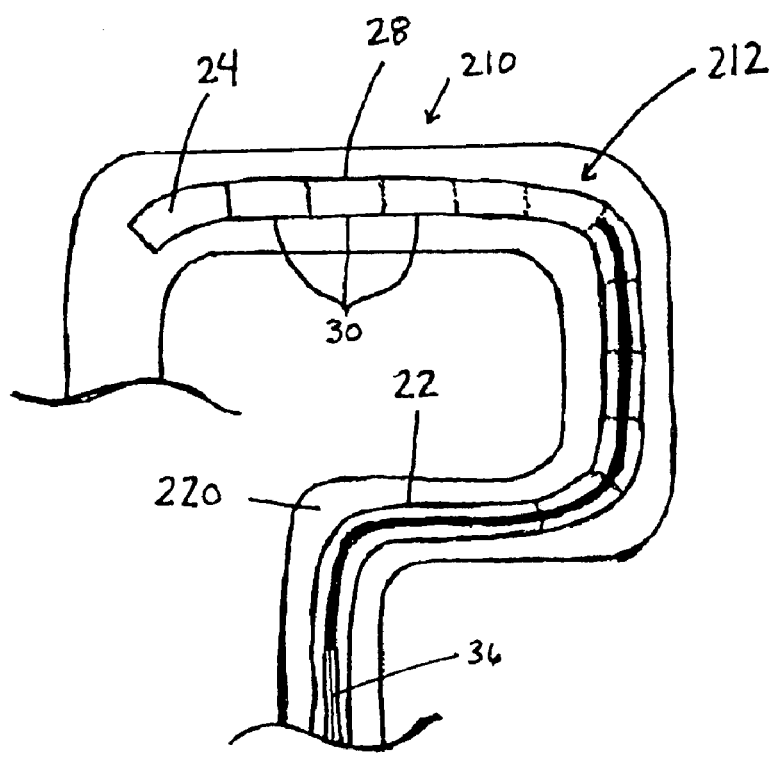

FIGS. 12A and 12B illustrate a variation of the endoscope advancing through a tortuous path, using an endoscope similar to the variation of FIG. 2B. FIG. 12A shows a pathway with multiple turns 210, resembling a length of the colon. The distal half of the device 212 comprises a steerable distal portion 24 and a controllable proximal portion 28. The guide 51 is slidably held within a lumen within the endoscope in the relaxed state. As the device 212 is advanced into the pathway 210, the user steers the distal tip 24, and the controllable segments 30 follow the curve selected by the user, navigating the chosen pathway. While in the relaxed state, the guide 51 may passively assume the shape taken by the distal portion 24 and the controllable proximal portion 28 as they are steered along the path. Usually, the user may rigidize and/or "lock" the guide 51 to assume the curve of the selected pathway before the controllable proximal portion 28 has advanced beyond the first curve 220. After being stiffened and locked into position, the endoscope can continue moving distally while still maintaining the selected pathway, since the passive flexible proximal region 22 of the endoscope slides over the rigid guide 51 and conforms to its shape, as shown in FIG. 12B.

After rigidizing the guide, the user can continue to steer the distal end 24 as it is advanced, and the curves of the selected pathway are propagated proximally down the controllable segments 30 as the endoscope moves forward. This variation of the device is capable of conforming to a selected pathway over the entire length of the endoscope, despite having a shorter guide 51 and controllable portion 28, since the combined length of the guide 51 and the controllable portion is preferably equal to the length of the endoscope.

Figure 13A:
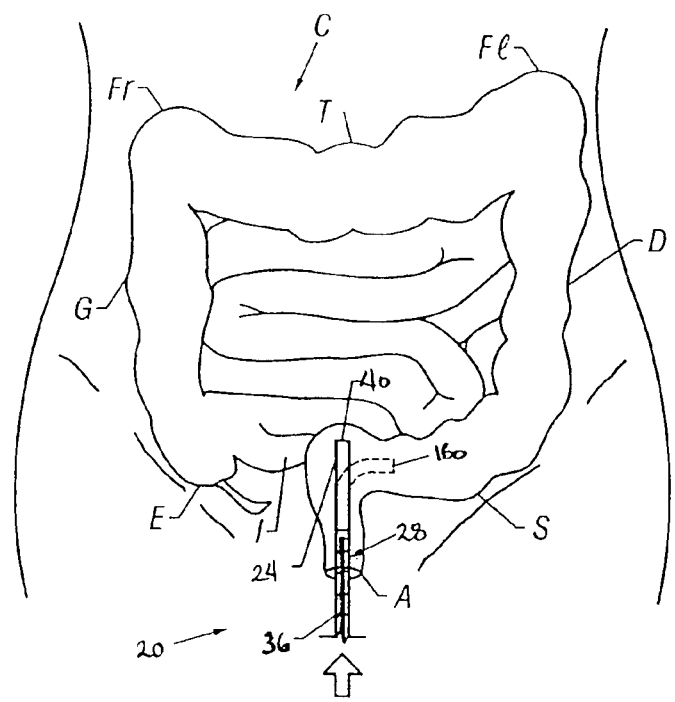
FIGS. 13A to 13H illustrate a representative example of advancing an endoscope through a patient's colon using a guiding apparatus to assist in advancing the endoscope.

In operation, any of the guiding apparatus as described above or one recognized by a person of skill in the art to be suitable for such use as described herein may be utilized. FIGS. 13A to 13H illustrate a representative method of advancing a colonscopic device 20 as described herein with a representative guide 36 for advancement into a patient's colon C. As seen in FIG. 13A, the steerable distal portion 24 of colonoscope 20 may be first advanced into the patient's rectum via anus A. The device 20 may be simply advanced, either manually or automatically by a motor, until the first curvature is reached or alternatively until the segments of controllable portion 28 are within colon C. At this point, the steerable distal portion 24 may be actively controlled by the physician or surgeon to attain an optimal curvature or shape for advancement of device 20. The optimal curvature or shape is considered to be the path which presents the least amount of contact or interference from the walls of colon C. If the optional controllable portion 28 is used with the colonoscopic device 20, once the advancement position 160 has been determined, the device 20 may be advanced further into the sigmoid colon S such that the automatically controlled segments of controllable portion 28 follow the distal portion 24 while transmitting the optimal curvature or shape proximally down the remaining segments of controllable portion 28.

Figure 13B:
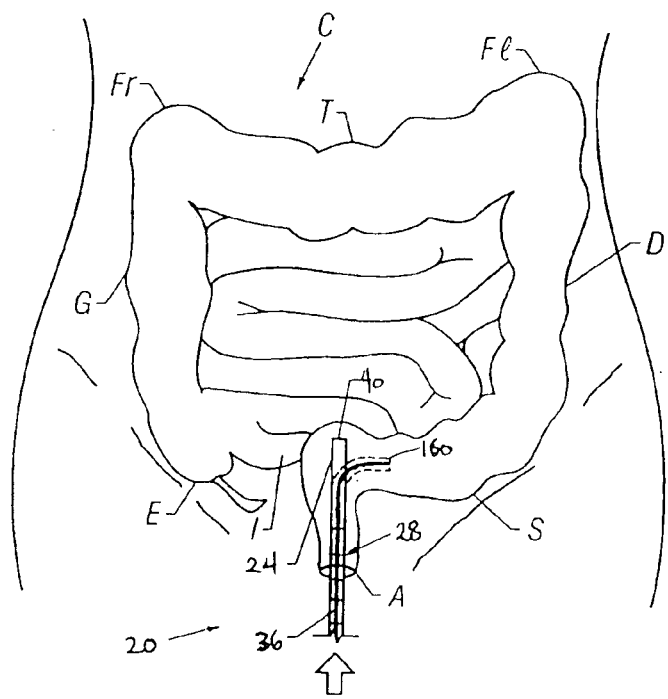

Alternatively, once steerable distal portion 24 has been steered or positioned for advancement 160, guide 36 may be advanced distally in its flexible state along or within device 20 until it reaches a distal position, i.e., some point distal of the flexible proximal portion 22 and preferably to the distal end of the device 20, as shown in FIG. 13B. Preferably, guide 36 is advanced to the distal end of steerable distal portion 24 or to the distal end of the optional controllable portion 28, if utilized, or to some point therebetween. Guide 36 may be advanced to any distal position as long as a portion of guide 36 attains the optimal curvature or shape. Prior to advancing the device 20 over guide 36, the guide 36 may be left in its flexible state or it may be optionally rigidized, as discussed above. If left in its flexible state, guide 36 will still provide desirable column strength to the device 20 as it is advanced through colon C over the guide 36. It is preferable, however, that guide 36 is rigidized once it has attained and conformed to the curvature. As the position of guide 36 is preferably rigidized and maintained, the device 20 may then be advanced over the guide 20 in a monorail or "piggy-back" fashion so that the flexible proximal portion 22 follows the curve held by guide 36 until the device 20 reaches the next point of curvature. The following description discusses the use of the optional controllable portion 28; however, this portion 28 may be omitted from the device 20.

Figure 13C:
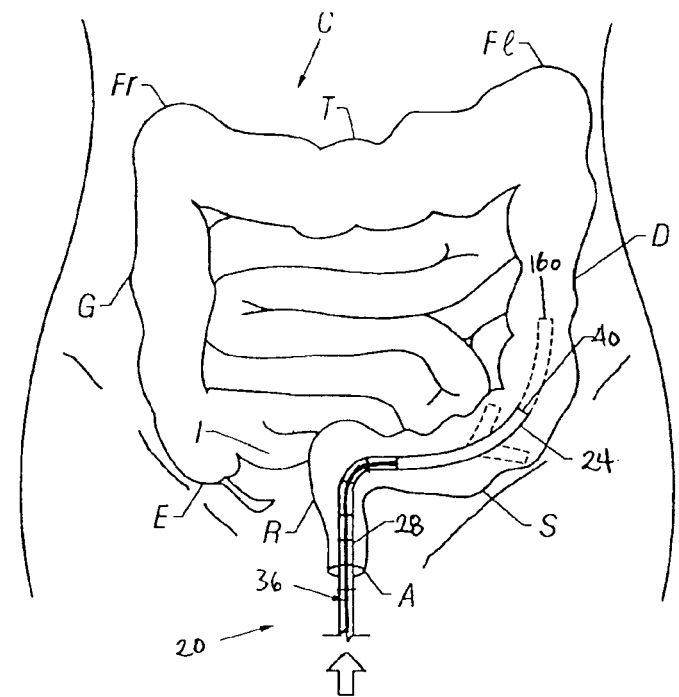
Figure 13D:
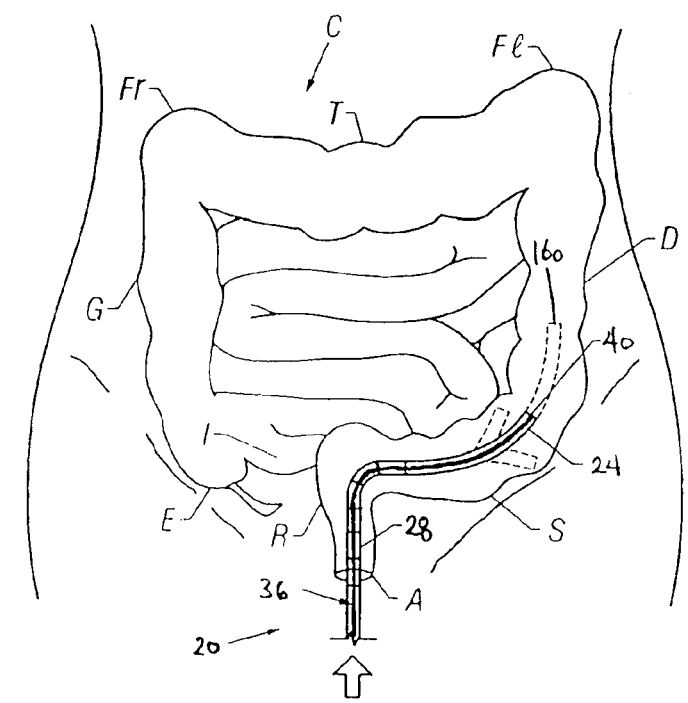

As shown from FIGS. 13B to 13C, the curve is maintained by guide 36 until the steerable distal portion 24 has been advanced to the juncture between the sigmoid colon S and the descending colon D. At this point, the distal portion 24 may be actively steered by the physician using a variety of visualization techniques, e.g., steering via an optional imaging bundle 40 located at the distal end of the device 20. Once the optimal curve or shape has been determined, the device 20 may be advanced to position 160. As the device is moved distally, if the controllable portion 28 is utilized, portion 28 will automatically follow the path set by the distal portion while the flexible proximal portion follows the device 20 along the curvature defined by the guide 36. Otherwise, if controllable portion 28 is omitted, guide 36 will have its curvature defined solely by steerable distal portion 24. Once the junction between the sigmoid colon S and descending colon D has been traversed by the steerable distal portion 24 and the optional controllable portion 28, the guide may then be relaxed and advanced distally along the device 20 in its flexible state until it reaches the distal position in the device 20. As the guide 36 is advanced, it will attain and conform to a new curvature defined by the steerable distal portion 24 and/or the controllable portion 28, as shown in FIG. 13D.

Figure 13E:
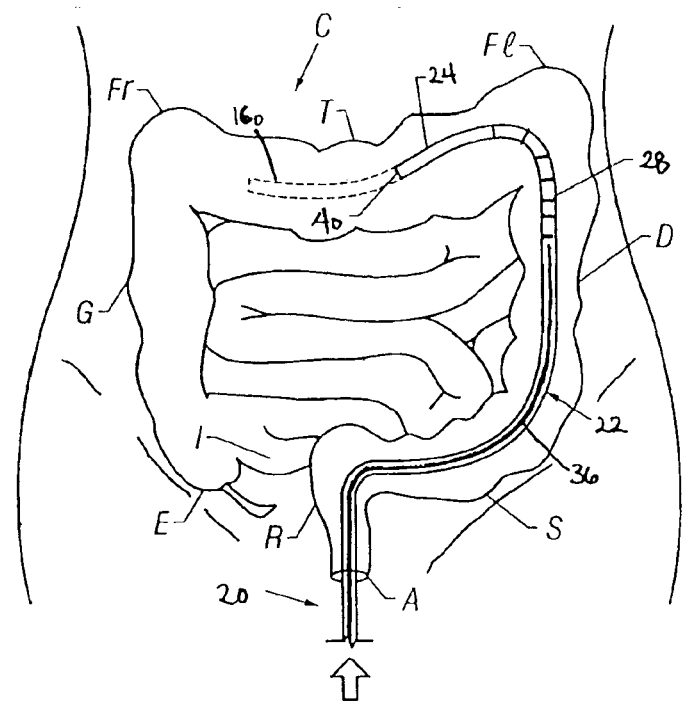
Figure 13F:
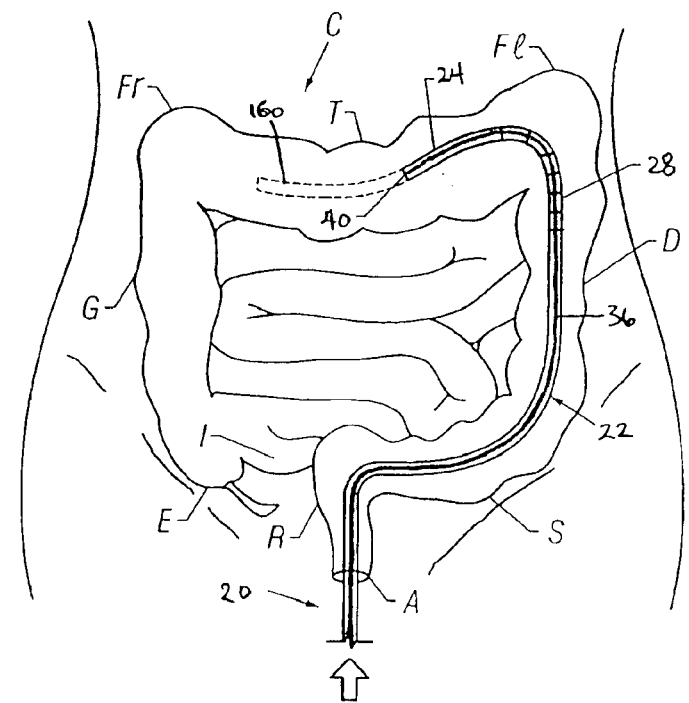
Figure 13G:
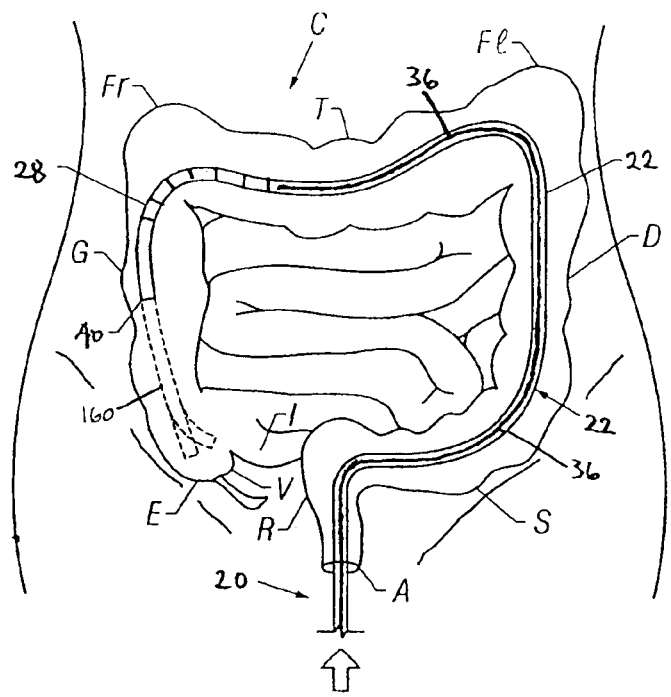

Having attained a new curvature, guide 36 may again be rigidized to maintain this shape. While the guide 36 maintains this shape, the device 20 may be advanced further distally along the descending colon D with the help of the rigidized guide 36 in the piggy-back manner described above to define the path for the flexible proximal portion 22 and to prevent excessive contact with the walls of colon C. As shown in FIG. 13E, the device 20 has been advanced past the left (splenic) flexure $F_1$ in the manner described above until the optional controllable portion 28 has attained the optimal curvature. The guide 36 may be relaxed again and advanced further distally in its flexible state, as shown from FIGS. 13E to 13F.

Figure 13H:
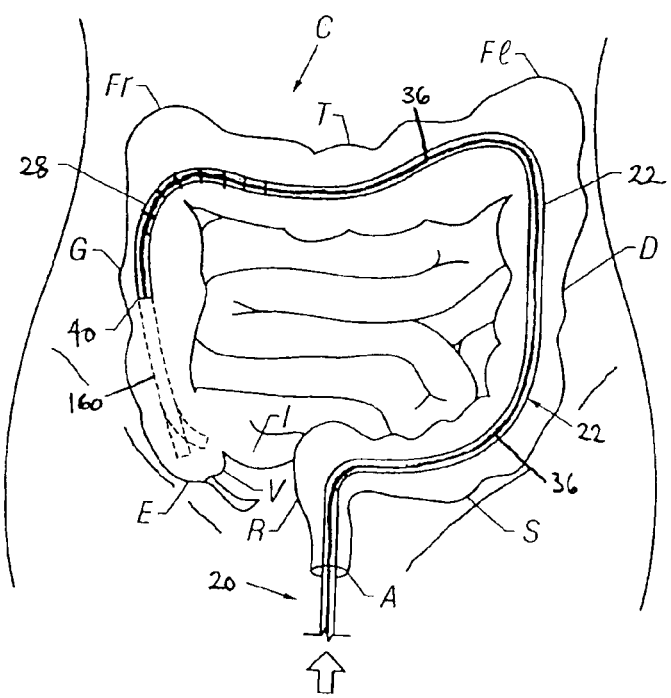

After guide 36 has assumed the desired curvature defined by the distal portion 24 and/or controllable portion 28, as shown in FIG. 13F, it may again be rigidized and the device 20 may then be advanced through the transverse colon T and around the right (hepatic) flexure $F_r$ in much the same manner as described above and as shown in FIG. 13G. Once the distal portion 24 and the optional controllable portion 28 has controllably negotiated past the right (hepatic) flexure $F_r$, the position of guide 20 may again be maintained while guide 36 is relaxed once again and advanced distally to assume the new curvature defined by distal portion 24 and/or controllable portion 28, as shown in FIG. 13H. After guide 36 is optionally rigidized again, device 20 may be advanced 160 completely within the ascending colon G towards the cecum E for a complete examination of the colon C with minimal complication and effort.

While the device 20 is advanced through the colon C, the physician or surgeon may stop the advancement to examine various areas along the colon wall using, e.g., the imaging bundle 40. During such examinations, the guide 36 may be temporarily withdrawn manually or automatically from the device 20 to allow for the insertion of other tools through the guide channel 50. After a procedure has been completed on the colon wall, the tool may be withdrawn from guide channel 50 and guide 36 may be reintroduced into the device 20 so that the device may optionally be advanced once again into colon C.

Figure 14A:
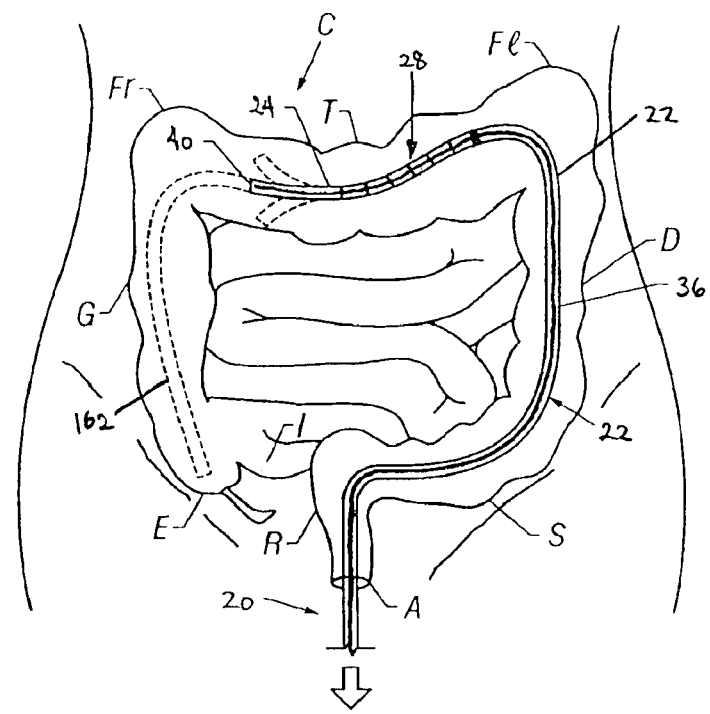
FIGS. 14A and 14B show a variation on the withdrawal of the endoscope with or without the guiding apparatus for the selective treatment of sites along the patient's colon.
Figure 14B:
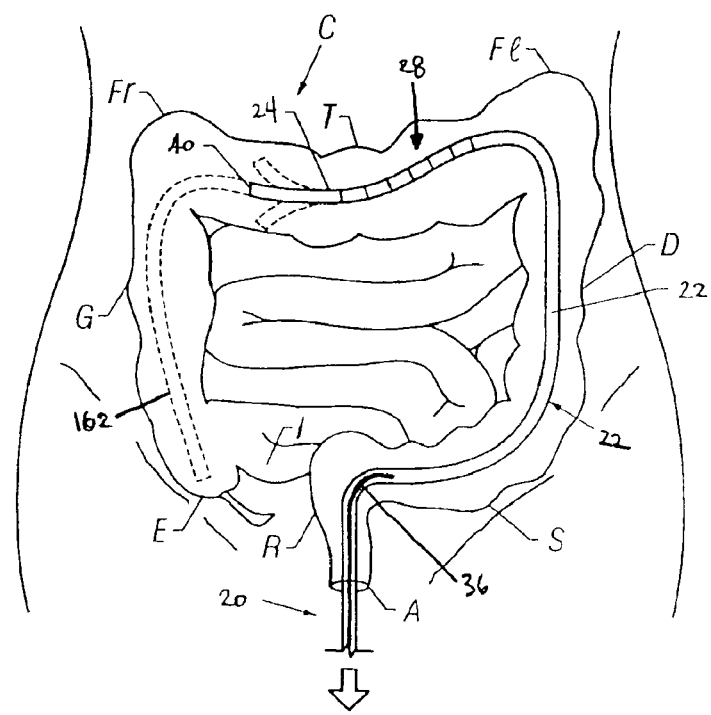

To withdraw device 20 from within the colon C, the procedure above may be reversed, as shown in FIG. 14A, such that the withdrawal 162 minimally contacts the walls of colon C. Alternatively, guide 36 may simply be removed from device 20, as shown in FIG. 14B, while leaving device 20 within colon C. The device 20 may simply be withdrawn by pulling the proximal portion 22 to remove the device 20. This method may rub or contact the device 20 upon the walls of colon C, but any impingement would be minimal.

Figure 15A:
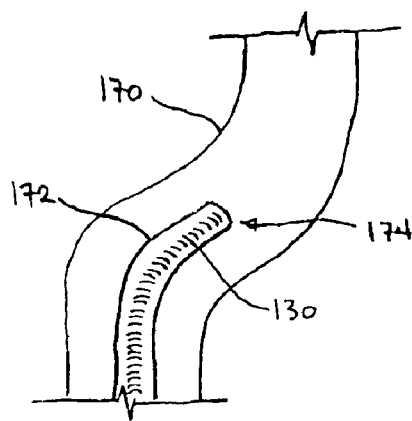
FIGS. 15A to 15C illustrate a representative example of advancing an endoscope through a tortuous path using the coaxial guiding apparatus shown in FIGS. 11A to 11C.
Figure 15B:
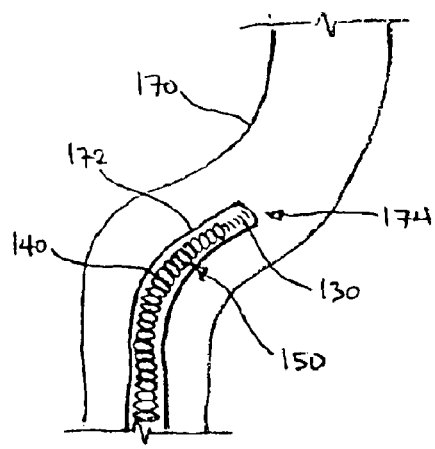
Figure 15C:
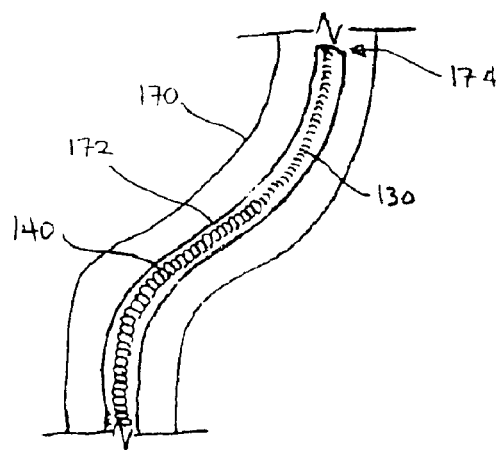

An alternative method of advancing an endoscope through a tortuous path may be seen in FIGS. 15A to 15C by using the rigidizable guide assembly 150 seen from FIG. 11C. FIG. 15A shows a pathway to be negotiated by endoscopic device 172. The pathway may represent a portion of colon 170. As device 172 is desirably steered to assume a curve, nested stiffening assembly 130 may be advanced distally within device 172 to distal end 174 while in a relaxed state. Alternatively, nested assembly 130 may be advanced in the flexible, relaxed state along with the distal end 174.

Once the curve has been selected, nested assembly 130 may be stiffened to maintain its shape. At this point, annular stiffening assembly 140 may be advanced over nested assembly 130 towards distal end 174. Once assembly 140 has assumed the curve defined by assembly 130, annular assembly 140 may then be rigidized and nested assembly 130 may be relaxed into its flexible state, as shown in FIG. 15B. Then the distal end 174 may be further advanced with or without assembly 130 while being pushed along the curve defined by rigidized annular assembly 140, as shown in FIG. 15C. Once distal end 174 of device 172 has negotiated the curve, nested assembly 130, after being advanced to distal end 174, may then be rigidized again and annular assembly 140 may be relaxed and advanced again over assembly 130 and so on until the desired treatment location has been reached within the body.

Figure 16A:
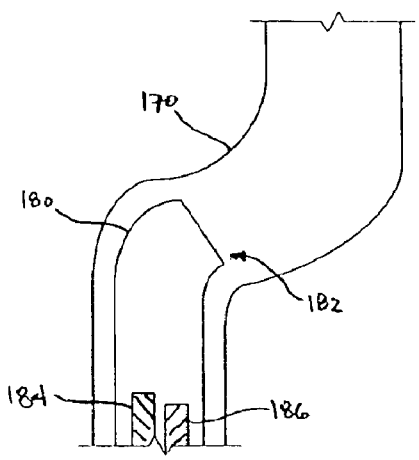
FIGS. 16A to 16E illustrate another variation of advancing an endoscope through a tortuous path using multiple guiding apparatuses.

Another alternative variation on advancing an endoscope through a tortuous path may be seen in FIGS. 16A to 16E. This variation uses multiple guides which may be alternately rigidized while being advanced distally along the path. FIG. 16A shows a portion of the curved pathway in colon 170 with endoscope 180 being advanced therethrough. Multiple guides may be used in this variation, but preferably two guides are utilized, as described below. Any one of the rigidizable guide variations discussed herein may be used solely or in combination with different types of guides in the same device 180. Each guide may be advanced within its own lumen defined within the endoscope, or they may also share a common dedicated lumen.

Figure 16B:
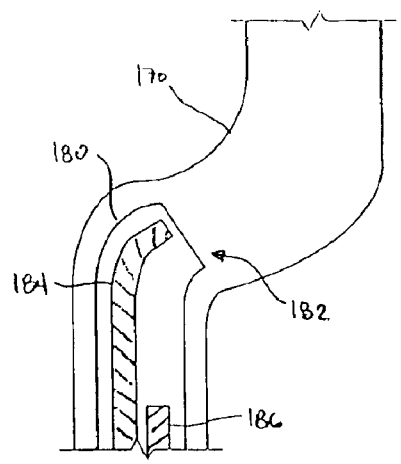

As device 180 approaches a curvature of colon 170, first guide 184 may be advanced towards the steerable distal end 182. While being advanced, first guide 184 is in a relaxed and flexible state allowing it to conform to the shape defined by the distal end 182. Having been advanced to distal end 182, as shown in FIG. 16B, first guide 184 is rigidized to maintain the shape defined by the steerable distal end 182. Device 180 may then be advanced further distally into colon 170 while riding over rigidized first guide 184.

Figure 16C:
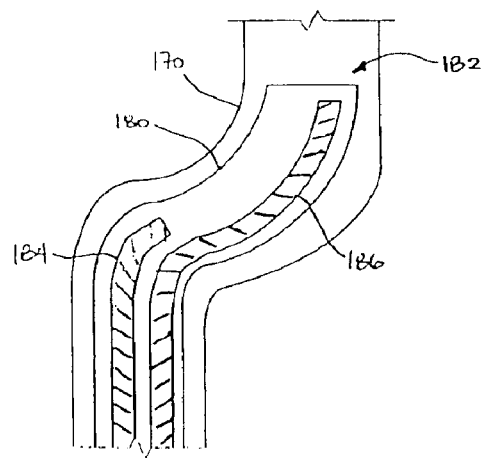
Figure 16D:
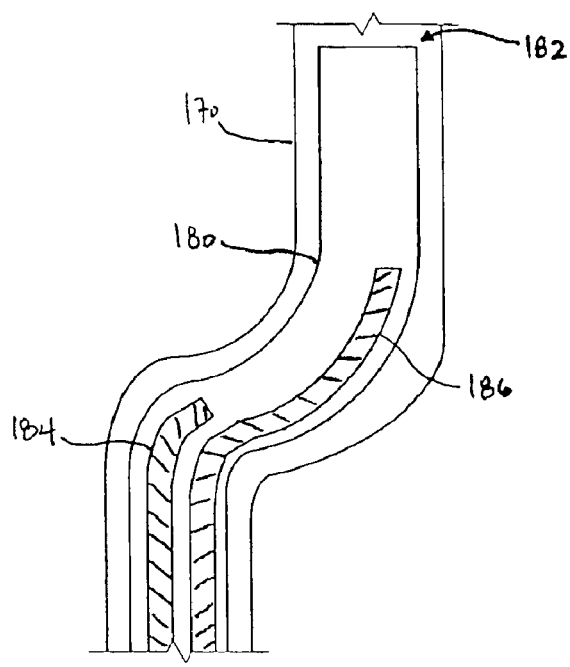

After device 180 has been further advanced to a new position, second guide 186 may also be advanced distally in its relaxed state through device 180 up to the distal end 182 while first guide 184 is preferably still rigidized, as shown in FIG. 16C. As second guide 186 advances, it may conform to a new shape defined by device 180. Second guide 186 may then be rigidized to hold its shape. First guide 184 may be relaxed but its rigid shape is preferably also maintained while the distal end 182 of device 180 is further advanced distally through colon 170, as shown in FIG. 16D.

Figure 16E:
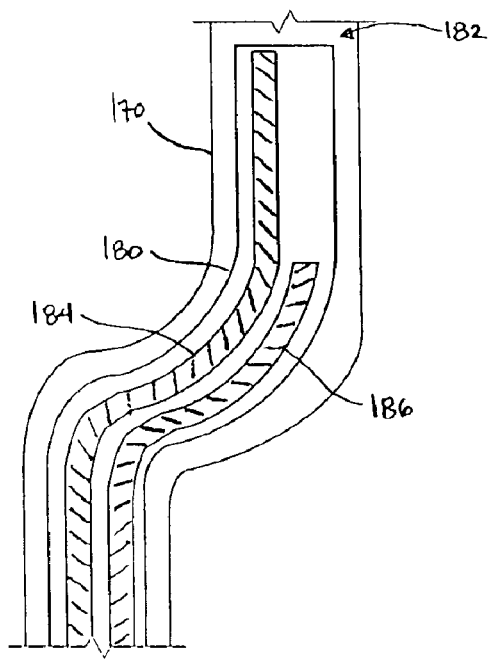

After device 180 has been advanced distally, first guide 184 may be relaxed and advanced through device 180 up to distal end 182 while the rigidity of second guide 186 is maintained, as shown in FIG. 16E. Second guide 186 may be relaxed and then advanced in its flexible state distally through device 180 and so on. This process may be repeated as device 180 is required to negotiate arbitrarily tortuous paths.

Although the endoscope of the present invention has been described for use as a colonoscope, the endoscope can be configured for a number of other medical and industrial applications. In addition, the present invention can also be configured as a catheter, cannula, surgical instrument or introducer sheath that uses the principles of the invention for navigating through tortuous body channels. The present invention may also be used for industrial applications such as inspection and exploratory applications within tortuous regions, e.g., machinery, pipes, etc.

In a variation of the method that is particularly applicable to laparoscopy or thoracoscopy procedures, the steerable endoscope can be selectively maneuvered along a desired path around and between organs in a patient's body cavity. The distal end of the endoscope may be inserted into the patient's body cavity through a natural opening, through a surgical incision or through a surgical cannula, introducer, or trocar. The selectively steerable distal portion can be used to explore and examine the patient's body cavity and to select a path around and between the patient's organs. The electronic motion controller in conjunction with the tracking rod can be used to control the automatically controlled proximal portion to follow the selected path and allow the rest of the body to follow the tracking rod and, if necessary, to return to a desired location using the three-dimensional model in the electronic memory of the electronic motion controller. Modification of the above-described assemblies and methods for carrying out the invention, and variations of aspects of the invention that are obvious to those of skill in the art are intended to be within the scope of the claims.

I claim:

1. A method of advancing an instrument along an arbitrary path, comprising:
   - selectively steering a distal portion of the instrument to assume a selected shape along an arbitrary path such that a portion of an elongate guide conforms to and assumes the selected shape;
   - advancing said instrument distally while configuring a controllable portion of said instrument to assume the selected shape of said distal portion, wherein said controllable portion is proximal to said distal portion: and
   - maintaining a position of said guide while advancing said instrument along said guide such that a proximal portion of said instrument assumes the selected shape defined by said guide, wherein said instrument is freely slidable along said guide such that advancing said instrument along said guide is unconstrained.

2. The method of claim 1 wherein prior to maintaining a position of said guide, further comprising advancing said instrument distally while configuring a controllable portion of said instrument to assume the selected shape of said distal portion, wherein said controllable portion is proximal to said distal portion.

3. The method of claim 1 wherein maintaining the position of said guide comprises rigidizing said guide such that said guide rigidly assumes a position of the selected shape.

4. The method of claim 3 wherein rigidizing said guide comprises applying tension to a tensioning member disposed within said guide such that a plurality of adjacent segments comprising said guide are compressed.

5. The method of claim 3 wherein rigidizing said guide comprises applying a vacuum force within a lumen defined within said guide such that a plurality of adjacent segments comprising said guide are compressed.

6. The method of claim 1 further comprising withdrawing said guide from said instrument.

7. The method of claim 1 wherein said guide is slidably located within said instrument through a lumen defined within the instrument.

8. A method of advancing an instrument along an arbitrary path, comprising:
   - providing an instrument having a proximal end, a controllable proximal portion, and a selectively steerable distal portion, and further providing an elongate guide having a distal portion positioned substantially adjacent to said distal portion of said instrument;
   - selectively steering said distal portion of said instrument to assume a selected shape along a desired path;
   - advancing said instrument distally along said desired path while controlling said controllable proximal portion to assume the selected shape of said distal portion such that said guide also assumes substantially the selected shape; and
   - maintaining a position of said guide while advancing said instrument along said guide such that a proximal portion of said instrument assumes the selected shaoe defined by said guide, wherein said instrument is freely slidable along a length of said guide such that advancing said instrument along the guide is unconstrained.

9. A method of advancing an instrument along an arbitrary path, comprising:
   - providing an instrument having a proximal end, a controllable proximal portion, and a selectively steerable distal portion, and further providing an elongate guide having a distal portion positioned substantially adjacent to said distal portion of said instrument;
   - selectively steering said distal portion of said instrument to assume a selected shape along a desired path;
   - advancing said instrument distally along said desired path while controlling said controllable proximal portion to assume the selected shape of said distal portion such that said guide also assumes substantially the selected shape; and
   - maintaining a position of said guide while advancing said instrument along said guide such that a proximal portion of said instrument assumes the selected shape defined by said guide, wherein said instrument is freely slidable along said guide such that advancing said instrument along the guide is unconstrained.

10. The method of claim 9 wherein maintaining the position of said guide comprises rigidizing said guide such that said guide rigidly assumes a position of the selected shape.

11. The method of claim 10 wherein rigidizing said guide comprises applying tension to a tensioning member disposed within said guide such that a plurality of adjacent segments comprising said guide are compressed.

12. The method of claim 10 wherein rigidizing said guide comprises applying a vacuum force within a lumen defined within said guide such that a plurality of adjacent segments comprising said guide are compressed.

13. An apparatus for insertion into a body cavity, comprising:
   - an elongate body having a selectively steerable distal portion adapted to assume a selected shape along an arbitrary path, a controllable proximal portion located proximal to said steerable distal portion, adapted to propagate the selected shape, and a flexible proximal portion proximal to said controllable proximal portion; and
   - an elongate guide having an axial length that is less than an axial length of said elongate body, wherein said guide is configured to conform to and selectively maintain the selected shape assumed by said steerable distal portion, and whereby the body is freely slidable along a length of the guide.

wherein said flexible proximal portion of said elongate body is adapted to conform to a selected shape maintained by said guide.

14. An apparatus for insertion into a body cavity, comprising:

an elongate body having a selectively steerable distal portion adapted to assume a selected shape along an arbitrary path, a controllable proximal portion located proximal to said steerable distal portion, adapted to propagate the selected shape, and a flexible proximal portion proximal to said controllable proximal portion; and an elongate guide having an axial length that is less than an axial length of said elongate body, wherein said guide is configured to conform to and selectively maintain the selected shape assumed by said steerable distal portion;

wherein said flexible proximal portion of said elongate body is adapted to conform to a selected shape maintained by said guide.

15. The apparatus of claim 14 wherein said axial length of said guide is approximately equal to a combined length of said controllable proximal portion and said steerable distal portion.

16. The apparatus of claim 14 wherein said elongate body defines a lumen therethrough.

17. The apparatus of claim 16 wherein said guide is slidably disposed within said lumen.

18. The apparatus of claim 14 wherein said selectively steerable distal portion is controllable via a control located externally of the body cavity.

19. The apparatus of claim 14 wherein said a length of said proximal controllable portion is approximately equal to half the length of said elongate body.

20. The apparatus of claim 14 wherein said proximal controllable portion comprises a plurality of pivotally connected segments.

21. The apparatus of claim 20 wherein each of said segments comprises an actuator for propagating the selected shape along said proximal controllable portion.

22. The apparatus of claim 21 wherein said actuator comprises a type of motor selected from the group consisting of pneumatic, hydraulic, electromechanical motors and drive shafts.

23. The apparatus of claim 21 wherein said actuator comprises a tendon.

24. The apparatus of claim 14 wherein said guide is configured to assume the selected shape when the guide is in a flexible state and wherein said guide is further configured to maintain the selected shape when the guide is in a rigidized state.

25. The apparatus of claim 24 wherein said guide is configured to selectively rigidize along the length of said guide to maintain the selected shape in the rigidized state.

26. The apparatus of claim 24 wherein the proximal section of said guide is in communication with a guide controller for selectively rigidizing the guide along its length.

27. The apparatus of claim 24 wherein said guide comprises a plurality of adjacent segments each defining a channel therethrough such that a common channel is defined through the length of the guide.

28. The apparatus of claim 27 further comprising a tensioning member disposed within said common channel such that applying a force to said tensioning member compresses said adjacent segments together.

29. The apparatus of claim 27 wherein said guide is configured to maintain a position of said adjacent segments relative to each other upon applying a vacuum force within said common channel.

30. The apparatus of claim 14 further comprising a suction device for withdrawing a gas from the body cavity through the elongate body.

31. The apparatus of claim 30 wherein the suction device is in fluid communication with a suction port defined on an outer surface of said elongate body.

32. The apparatus of claim 30 wherein said suction device is controllable via a controller located externally of the body cavity.

33. An apparatus for inserting into a body cavity comprising:

an elongate body having a proximal portion and a selectively steerable distal portion and defining a lumen therebetween, the steerable distal portion being configurable to assume a selected shape along an arbitrary path;

a suction device for withdrawing gas from the body cavity and through the elongate body, wherein the suction device is in fluid communication with a suction port defined on an outer surface of said elongate body;

an elongate guide having a proximal section, a distal section, and a length therebetween, said guide being slidably disposed without constraint within said lumen along the length for selectively supporting said body, wherein said guide is configured to conform to and selectively maintain the selected shape assumed by said steerable distal portion, and wherein said proximal portion of said elongate body when advanced distally is configured to conform to the selected curve maintained by said guide.

* * * * *